US005767362A

United States Patent [19]
Best et al.

[11] Patent Number: 5,767,362
[45] Date of Patent: Jun. 16, 1998

[54] METHODS AND COMPOSITIONS FOR MODULATING LIPID CONTENT OF PLANT TISSUES

[75] Inventors: Elaine A. Best, Davis; Vic C. Knauf, Winters, both of Calif.

[73] Assignee: Calgene, Inc., Davis, Calif.

[21] Appl. No.: 74,121

[22] Filed: Jun. 8, 1993

[51] Int. Cl.⁶ .............................. A01H 5/00; C12N 5/04; C12N 15/82
[52] U.S. Cl. .................... 800/205; 435/69.1; 435/172.3; 435/320.1; 435/419; 536/23.7
[58] Field of Search ........................ 800/205, DIG. 17; 435/69.1, 134, 172.3, 240.4, 240.49, 320.1, 419; 536/23.1, 23.7

[56] References Cited

U.S. PATENT DOCUMENTS

| | | | |
|---|---|---|---|
| 4,943,674 | 7/1990 | Houck et al. | 800/205 |
| 5,106,739 | 4/1992 | Comai et al. | 435/172.3 |
| 5,175,095 | 12/1992 | Martineau et al. | 435/69.1 |
| 5,539,092 | 7/1996 | Haselkorn et al. | 536/23.2 |

FOREIGN PATENT DOCUMENTS

| | | |
|---|---|---|
| 0 255 378 | 2/1988 | European Pat. Off. . |
| 0255378 | 2/1988 | European Pat. Off. . |
| 0 409 625 | 1/1991 | European Pat. Off. . |
| 0 409 629 | 1/1991 | European Pat. Off. . |

OTHER PUBLICATIONS

Boyer (Ed), *The Enzymes*, 3rd ed., vol. 6, (1979).

Post–Beittenmiller et al., "In Vivo Pools of Free and Acylated Acyl Carrier Proteins in Spinach", *J. Biol. Chem.*, vol. 266, pp. 1858–1865 (1991).

Comai et al., "Chloroplast Transport of a Ribulose Bisphosphate Carboxylase Small Subunit–5–Enolpyruvyl 3–Phosphoshikimate Synthase Chimeric Protein", *J. Biol. Chem.*, vol. 263, pp. 15104–15109, (1988).

Turnham et al., "Changes in the Activity of Acteyl–CoA Carboxylase During Rape–seed Formation", *Biochem. J.*, vol. 212, pp. 223–229, (1983).

Al–Feel et al., "Cloning of the Yeast FAS3 Gene and Primary Structure of Yeast Acetyl–CoA Carboxylase", *Proc. Natl. Acad. Sci.*, vol. 89, pp. 4534–4538, (1992).

Lopez–Casillas et al., "Structure of the Coding Sequence and Primary Amino Acid Sequence of Acetyl–coenzyme A Carboxylase", *Proc. Natl. Acad. Sci. USA*, vol. 85, pp. 5784–5788, (1988).

Slabas et al., "The Basic Polypeptide Subunit of Rape Leaf Acetyl–CoA Carboxylase is a 220kDa Protein", *Soc. Trans. Lond.*, vol. 14, p. 716, (1986).

Slabas et al., "Rapid Purification of a High Molecular Weight Subunit Polypeptide Form of Rape Seed Acetyl CoA Carboxylase", *Plant Science*, vol. 39, pp. 177–182, (1985).

Kondo et al., "Acetyl–CoA Carboxylase from *Escherichia coli*: Gene Organization and Nucleotide Sequence of the Biotin Carboxylase Subunit", *Proc. Natl. Acad. Sci. USA*, vol. 88, pp. 9730–9733, (1991).

Voelker et al., "Fatty Acid Biosynthesis Redirected to Medium Chains in Transgenic Oilseed Plants", *Science*, vol. 257, pp. 72–74, (1992).

Browse et al., "Fatty Acid Composition of Leaf Lipids Determined after Combined Digestion and Fatty Acid Methyl Ester Formation from Fresh Tissue", *Anal. Biochem.*, vol. 152, pp. 141–145, (1986).

Li et al., "Putative Zinc Finger Protein Encoded by a Conserved Chloroplast Gene is very Likely a Subunit of a Biotin–dependent Carboxylase", *Plant Molec. Biol.*, vol. 20, pp. 759–761, (1992).

McBride et al., "Improved Binary Vectors for *Agrobacterium* –mediated Plant Transformation", *Plant Molec. Biol.*, vol. 14, pp. 269–276, (1990).

Egin–Buhler et al., "Improved Purification and Further Characterization of Acetyl–CoA Carboxylase from Cultured Cells of Parsley", *Eur. J. Biochem.*, vol. 133, pp. 335–339, (1983).

Numa (Ed.), "Acetyl–coenzyme A Carboxylase and its Regulation", *Fatty Acid Metabolism and Its Regulation*, pp. 1–27, (1984).

An et al., "New Cloning Vehicles for Transformation of Higher Plants", *EMBO J.*, vol. 4, pp. 277–284, (1985).

Bolivar et al., "Construction and Characterization of New Cloning Vehicles", *Gene*, vol. 2, pp. 95–113, (1977).

Chang and Cohen, "Construction and Characterization of Amplifiable Multicopy DNA Cloning Vehicles Derived from the P15A Cryptic Miniplasmid", *J. Bacteriol.*, vol. 134, pp. 1141–1156, (1978).

Comai et al., "Expression in Plants of a Mutant aroA Gene from *Salmonella typhimurium* Confers Tolerance to Glyphosate", *Nature*, vol. 317, pp. 741–744, (1985).

Comai et al., "An Altered aroA Gene Product Confers Resistance to the Herbicide Glyphosate", *Science*, vol. 221, pp. 370–371, (1983).

Coruzzi et al., "Nucleotide Sequences of Two Pea cDNA Clones Encoding the Small Subunit of Ribulose 1,5–Biophosphate Carboylase", *J. Biol. Chem.*, vol. 258, pp. 1399–1402, (1983).

(List continued on next page.)

*Primary Examiner*—Elizabeth F. McElwain

[57] ABSTRACT

Novel compositions and methods are provided for modifying the lipid content of plant tissues of interest, including leaf, root, fruit and seed. The methods involve transforming a plant cell of interest with an expression cassette functional in a plant cell comprising a transcriptional and translational initiation regulatory region, joined in reading frame 5' to a DNA sequence encoding an enzyme capable of modulating the production of fatty acids, and translational and transcriptional termination regions. Expression of the enzyme provides for an increase in fatty acid biosynthesis as a result of altered concentrations of substrate for enzymes involved in fatty acid biosynthesis. Of particular interest is the selective control of lipid production in plant tissues such as leaves, root, fruit and seed.

30 Claims, 14 Drawing Sheets

OTHER PUBLICATIONS

Dunsmuir et al., "A Number of Different Nuclear Genes for the Small Subunit of RuBPCCase are Transcribed in Petunia", *Nucleic Acids Res.*, vol. 11, pp. 4177–4183, (1983).

Gardner et al., "The Complete Nucleotide Sequence of an Infectious Clone of Cauliflower Mosaic Virus by M13mp7 Shotgun Sequencing", *Nucleic Acids Res.*, vol. 9, pp. 2871–2888, (1981).

Horsch et al., "A Simple and General Method for Transferring Genes into Plants", *Science*, vol. 227, pp. 1229–1231, (1985).

Jorgensen et al., "A Restriction Enzyme Cleavage Map of Tn5 and Location of a Region Encoding Neomycin Resistance", *Mol. Gen. Genet.*, vol. 117, pp. 65–72, (1979).

Kannangara and Stumpf, "Fat Metabolism in Higher Plants", *Archives of Biochem. and Biophys.*, vol. 152, pp. 83–91, (1972).

Laemmli, "Cleavage of Structural Proteins during the Assembly of the Head of Bacteriophage T4", *Nature*, vol. 227, pp. 680–685, (1970).

Li and Cronan, Jr., "The Genes Encoding the Two Carboxyltransferase Subunits of *Escherichia coli* Acetyl–CoA Carboxylase", *J. Biol. Chem.*, vol. 267, pp. 16841–16847, (1992).

Knauf et al., *Molecular Genetics of the Bacteria–Plant Interaction*, p. 245, (1983).

Melton et al., "Efficient In Vitro Synthesis of Biologically Active RNA and RNA Hybridization Probes from Plasmids Containing a Bateriophage SP6 Promoter", *Nucleic Acid Research*, vol. 12, pp. 7035–7056, (1984).

Messing and Vieira, "A New Pair of M13 Vectors for Selecting Either DNA Strand of Double–Digest Restriction Fragments", *Gene*, vol. 19, pp. 269–276, (1982).

Muramatsu and Mizuno, "Nucleotide Sequence of the fabE Gene and Flanking Regions Containing a Bent DNA Sequence of *Escherichia coli*", *Nucleic Acids Research*, vol. 17, p. 3982, (1989).

Pear et al., "Isolation and Characterization of a Fruit–Specific cDNA and the Corresponding Genomic Clone from Tomato", *Plant Mol. Biol.*, vol. 13, pp. 639–651, (1989).

Pokalsky et al., "Structure and Expression of Elongation Factor 1alpha in Tomato", *Nucleic Acids Research*, vol. 17, pp. 4661–4673, (1989).

Sanger et al., "Characteristics of a Strong Promoter from Figwort Mosaic Virus: Comparison with the Analogous 35S Promoter from Cauliflower Mosaic Virus", *Plant Mol. Biol.*, vol. 14, pp. 433–443, (1990).

Stalker et al., "A Single Amino Acid Substitution in the Enzyme 5–Enolpyruvylshikimate–3–phosphate Synthase Confers Resistance to the Herbicide Glyphosate", *J. Biol. Chem.*, vol. 260, pp. 4724–4728, (1985).

Towbin et al., "Electrophoretic Transfer of Proteins from Polyacrylamide Gels to Nitrocellulose Sheets: Procedure and Some Applications", *Proc. Natl. Acad. Sci. USA*, vol. 76, pp. 4350–4354, (1979).

Post–Beittenmiller et al (1989) The Plant Cell 1: 889–899.

Kay et al (1987) Science 236: 1299–1302.

Knauf, V.C. (1987) Tibtech 5: 40–47.

Axtell, J.D. (1981) In *Plant Breeding II* (K.J. Frey, ed.), Iowa State Univ. Press, Ames, IA pp. 365–414 (Chapter 10).

Goodwin and Mercer (1983) Introduction to Plant Biochemistry, $2^{nd}$ ed. Pergamon Press, Oxford, p. 45.

```
  1 GATACTCCACTAAACAGCTATTATTGATACGCCCTCCGTCGCCTGTTAGGTTTATGTTGCCTTTGCCTGGG    69
 70 CGcTACGCTTAGCCCCCTTACTTATTTCTGGTACCATGGGTGaATAATCTGATTTTGTTGACTACAAA  138
139 TTAATCACTCGAACCTATTTAATGCTGAGCATTGTCAATCGTTAATTTGCGTGCTTTAGCATTCACA   207
208 TCTATCCAGAGACGATGCAGTGAAAAATTGGGTAATCCCCACATTATTTGTGTCTGTGAAGATTATCTTCAGCCCCCTCATCTTGTC 276
277 GCGATCCTGGCATCCCTACATTATTTGTGTCTGTGAAGATTATCTCATTGCAGCCCCCTCATCTTCGCA  345
346 GgGCTGTGGCTTTTTCAGCTTTTCACCTTACGTTATAAGAAGTTCCGTCGATGATGGGCTAATTTCGTGAA 414
415 TTGTGCGGCTTGTTGCAATTACACGGTGTTGAAGGTTATTTCATAGTTAGCTGTTGATTATCTTCCCTG  483
484 ATAAGACCAGTATTTAGCTGCCAATTGCTACGAAATCGTTATAATGTGCGACCTCGTCCTCCCCTGACGC 552
553 AGTTTTTGCGCTGCGGAAAAAGGTGACATTGGCGCAACGAAGGTATATTTGTTTTTTGCCGGAGGATAG  621
622 CAGCAGATCGCTGCACAATGTCCGTCAAGTCTAACATTGACACTCTGGGGCAAAATAGACCGGCGTCCC  690
691 GGCCTGCTGGAATTTATCGCTATGCATACAGCTGTCGGGGCATACGCTTTACAGACGGGCGGTGAAACGC 759
```

FIG. 3A

```
760   CTGTCACAATCACACTAAACAAAGAGTACGGAACCCACTCATGGATATTCGTAAGATTAAAAAACTGAT   828
                                      METAspIleArgLysIleLysLysLeuIl

829   CGAGCTGGTTGAAGAATCAGGCATCTCCGAACTGGAAATTCTGAAGGCGAAGAGTCAGTACGCATTAG   897
      eGluLeuValGluGluSerGlyIleSerGluLeuGluIleSerGluLeuGluSerValArgIleSe

898   CCGTGCAGCTCCTGCCGCAAGTTTCCCTGTGATGCAACAAGCTTACGCTGCACCAATGATGCAGCAGCC   966
      rArgAlaAlaProAlaAlaSerPheProValMETGlnAlaTyrAlaAlaProMETMETGlnGlnPr

967   AGCTCAATCTAACGCAGCCGCTCCGGCGACCGTTCCTCCATGGAAGCCAGCAGCAGCGGAAATCAG    1035
      oAlaGlnSerAsnAlaAlaAlaProAlaThrValProSerMETGluAlaAlaAlaGluIleSe

1036  TGGTCACACATCGTACGTTCCCCGATGGTTGGTACTTTCTACCGCACCCCAAGCCCGGACGCAAAAGCGTT  1104
      rGlyHisIleValArgSerProMETValGlyThrPheTyrArgThrProSerProAspAlaLysAlaPh

1105  CATCGAAGTGGGTCAGAAAGTCAACGTGGGCGATACCCTGTGCATCGTTGAAGCCATGAAAATGATGAA  1173
      eIleGluValGlyGlnLysValAsnValGlyAspThrLeuCysIleValGluAlaMETLysMETMETAs

1174  CCAGATCGAAGCGGACAAATCCGGTACCGTGAAAGCAATTCTGGTCGAAAGTGGACAACCGGTAGAATT  1242
      nGlnIleGluAlaAspLysSerGlyThrValLysAlaIleLeuValGluSerGlyGlnProValGluPh
```

FIG. 3B

```
1243  TGACGAGCCGCTGTCGTCATCGAGTAACGAGGCGAACATGCTGGATAAAATTGTTATTGCCAACCGCG  1311
         eAspGluProLeuValValIleGlu    METLeuAspLysIleValIleAlaAsnArgG

1312  GCGAGATTGCATTGCCTATTCTTCGTGCCTGTAAAGAACTGGGCATCAAGACTGTCGCTGTGCACTCCA  1380
      lyGluIleAlaLeuArgIleLeuArgAlaCysLysLysGluLeuGlyIleLysThrValAlaValHisSerS

1381  GCGCGGGATCGCGATCTAAAACACGTATTACTGGCAGATGAAACGGTCTGTATTGGCCCTGCTCCGTCAG  1449
      erAlaAspArgAspLeuLysHisValLeuLeuAlaAspGluThrValCysIleGlyProAlaProSerV

1450  TAAAAAGTTATCTGAACATCCCGGCAATCATCAGCGCCGCTGAAATCACCGGCAGTAGCAATCCATC   1518
      alLysSerTyrLeuAsnIleProAlaIleIleSerAlaAlaGluIleThrGlyAlaValAlaIleHisP

1519  CGGGTTACGGCTTCCTCTCCGAGAACGCCAACTTTGCCGAGCAGGTTGAACGCTCCGGCTTTATCTTCA  1587
      roGlyTyrGlyPheLeuSerGluAsnAlaAsnPheAlaGluGlnValGluArgSerGlyPheIlePheI

1588  TTGGCCCGAAAGCAGAAACCATTCGCCTGATGGGCGACAAAGTATCGGCAATCGCGGCGATGAAAAAAG  1656
      leGlyProLysAlaGluThrIleArgLeuMETGlyAspLysValSerAlaIleAlaAlaMETLysLysA

1657  CGGGCGTCCCTTGCGTACCGGGTTCTGACGGCCCGCTGGGCGACGATATGGATAAAAACCGTGCCATTG  1725
      laGlyValProCysValProGlySerAspGlyProLeuGlyAspAspMETAspLysAsnArgAlaIleA
```

FIG. 3C

```
1726  CTAAACGCATTGGTTATCCGGTGATTATCAAAGCCTCCGGCGGCGGCGGTCGCGGTATGCGCGTAG  1794
      laLysArgIleGlyTyrProValIleIleLysAlaSerGlyGlyGlyGlyArgGlyMETArgValV

1795  TGCGCGGGCGACGCTGAACTGGCACAATCCATCTCCATGACCCGTGCGGAAGCGAAAGCTGCTTCAGCA  1863
      alArgGlyAspAlaGluLeuAlaGlnSerIleSerMETThrArgAlaGluAlaLysAlaAlaPheSerA

1864  ACGATATGGTTTACATGGAGAAATCCTGGAAAATCCTCGCCACGTCGAGATTCAGGTACTGGCTGACG  1932
      snAspMETValTyrMETGluLysTyrLeuGluAsnProArgHisValGluIleGlnValLeuAlaAspG

1933  GTCAGGGCAACGCTATCTATCTGGCGGAACGTGACTGCTCCATGCAACGCCGCCACCAGAAAGTGGTCG  2001
      lyGlnGlyAsnAlaIleTyrLeuAlaGluArgAspCysSerMETGlnArgArgHisGlnLysValValG

2002  AAGAAGCGCCAGCACCGGGCATTACCCCGGAACTGCTGCGCTACATCGGCGAACGTTGCGCTAAAGCGT  2070
      luGluAlaProAlaProGlyIleThrProGluLeuLeuArgTyrIleGlyGluArgCysAlaLysAlaC

2071  GTGTTGATATCGGCTATCGCGGTGCAGGTACTTTCGAGTTCCTGTTCGAAAACGGCGAGTTCTATTTCA  2139
      ysValAspIleGlyTyrArgGlyAlaGlyThrPheGluPheLeuPheGluAsnGlyGluPheTyrPheI

2140  TCGAAATGAACACCCGTATTCAGGTAGAAcACCCGGTTACAGAAATGATCACCGGCGTTGACCTGATCA  2208
      leGluMETAsnThrArgIleGlnValGluHisProValThrGluMETIleThrGlyValAspLeuIleL
```

```
2209  AAGAACAGCTGCGTATCGCTGCCGGTCAACCGCTGTCGATCAAGCAAGAAGAAGTTCACGTTCGCGGCC  2277
      ysGluGlnLeuArgIleAlaAlaGlyGlnProLeuSerIleLysGlnGluValHisValArgGlyH

2278  ATGCGGTGGAATGTCGTATCAACGCCGAAGATCCGAACACCTTCCTGCCAAGTCCCGGCAAAATCACCC  2346
      isAlaValGlyCysArgIleAsnAlaGluAspProAsnThrPheLeuProSerProGlyLysIleThrA

2347  GTTTCCACGCACCTGGCGGTTTGGCGTACGTTGGGAGTCTCATATCTACGCGGGCTACACCGTACCGC  2415
      rgPheHisAlaProGlyGlyPheGlyValArgTrpGluSerHisIleTyrAlaGlyTyrThrValProP

2416  CGTACTATGACTCAATGATCGGTAAGCTGATTTGCTACGGTGAAAACCGTGACGTGGGCGATTGCCCGCA  2484
      roTyrTyrAspSerMETIleGlyLysLeuIleCysTyrGlyGluAsnArgAspValAlaIleAlaArgM

2485  TGAAGAATGCCTGCAGGAGCTGATCATCGACGGTATCAAAACCAACGTTGATCTGCAGATCCGCATCA  2553
      ETLysAsnAlaLeuGlnGluLeuIleIleAspGlyIleLysThrAsnValAspLeuGlnIleArgIleM

2554  TGAATGACGAGAACTTCCAGCATGGTGGCGGTACTAACATCCACTATCTGGAGAAAAAACTCGGTCTTCAGG  2622
      ETAsnAspGluAsnPheGlnHisGlyGlyThrAsnIleHisTyrLeuGluLysLysLeuGlyLeuGlnG

2623  AAAAATAAGACTGCTAAAGGCGTCAAAAGGCCGGATTTTCCGGCCTTTTTTATTACTGGGATCGACAAC  2691
      luLys

2692  CCCCATAAGGTACAATCCCCGCTTTCTTCACCCATCAGGGACAAAAATGGACACTCGTTTTGTTCAGG  2760
```

```
2761  CCCATAAAGAGGCGCGCTGGGCGTGGGCTGACCCCTTTTGTATCTGGCAGTTTGGTTAGTAGCCGCTTTa  2829
2830  CTTATCTGGCGTTGCCCCCGGTTTACCGGCTTTCCCGCTGGTTTGAGATGGCCTGCATCCTGACGCC  2898
2899  GCTGCTGTTTATTGGACTGTGCTGGGCGATGGTGAAATTTATCTATCGCGATATCCCACTGGAGGATGA  2967
2968  CGATGCAGCTTGAAGTAATTCTACCGCTGGTCGCCTATCTGGTGGTGGTTCGGTATCTCGGTTTATG  3036
3037  CGATGCGTAAACGGAGCACCGGCACCTTCCTTAATGAGTAT  3077
```

FIG. 3F

```
  1  CATCGAGCGGCCAGGTTCTCACCGATCCCACGGTGCAGGCACGACTGCCGGCCTACCGCCTGCGCTT   69
 70  CGACATCACCGAAAGCAACCCGGCCAGCGCGGCCCTGCTGGACCGCTACAACCTGTTCGGTCCGCCGGC  138
139  GATCCCTGTTCTTCGCCCCGGGGCTCGCCGAACGACTGCGCCGGGCCGGTGACGAATGGAGCGACTTGCGGCGTCATCGGAGAGATCGACGCCGC  207
208  CGGGCTCGCCGAACATGCGGCCCGGCCCGGCGATCTACTGCAATCTAACAGTGACTGGACAGTCATACGGAAATTCCGGCA  276
277  TTGCCGGTCAACATGCGGCCCGGCCCGGCGATCTACTGCAATCTAACAGTGACTGGACAGTCATACGGAAATTCCGGCA  345
346  TAGTGCCCGCTTGCCGTTTGCAGCCTGTACAGGACAATCAACAAGACAATGGCGACCCCTCGTATTG  414
415  CACGGGCCGAATCTGAACCTGCTGGGCCACCCGCGAGCCCGGCCACCTACGGTTCGACCACCCTCGGGCAG  483
484  ATCAACCAGGACCTCGAGCGCGGCCCGCCGGAAGCCGCCACCTGCTGCATCTGCAGAGCAACGCC  552
553  GAATACGAACTGATCGACCGGATCCATGCCGCGGCCGACGAAGGCGTGGACTTCATCATCATCAATCCG  621
622  GCGGCATTCACCCATACCAGCGTCGCGTTACGTGACGCGCTGCGGTGAGCATCCCATTCATCGAA  690
691  GTGCACCTGTCGAACGTGCACAAACGTGAACCTTTCCGGCATCACTCCTACTTCTCCGACGTGGCGGTA  759
```

```
1312  CGCTGTTCACCATCGTCTAAGCCCGGGGGGAACCTGCGATGTTGGAAAAAGTGCTGATCGCCAACCGCGG  1380
      roLeuPheThrIleVal .           METLeuGluLysValLeuIleAlaAsnArgGl

1381  CGAAATCGCCTTGCCATCCTTCGCGCATGCAAGGAGCTGGGGATCAAGAAGACGGTGGCGTACACTCCAC  1449
      yGluIleAlaLeuArgIleLeuGlyIleLysThrValAlaValHisSerTh

1450  CGCCGACCGCGAGTTGATGCACTGTCGCCTCGCCGACGAATCGGTTGTGTGCATCGTCCGGTCCGGCCAC  1518
      rAlaAspArgGluLeuMETHisLeuSerLeuAlaAspGluSerValCysIleGlyProAlaProAlaTh

1519  CCAGTCGTACCTGCAGATCATCCCGGCGATCATCGCCGAGGTCACCGGCGCCACCGGCGATCCACCC  1587
      rGlnSerTyrLeuGlnIleProAlaIleIleAlaAlaAlaGluValThrGlyAlaThrAlaIleHisPr

1588  CGGCTACGGCTTCCTCGCGGAGAACGCCGACTTCGCCGAGCAGATCGAACGCTCCGGCTTCACCTTCGT  1656
      oGlyTyrGlyPheLeuAlaGluAsnAlaAspPheAlaGluGlnIleGluArgSerGlyPheThrPheVa

1657  CGGCCCGACCGGCGAGGTGATCCGCCTGATGGGCGACAAGGTTTCGGCCAAGGACGCCATGAAGCGCGC  1725
      lGlyProThrGlyGluValIleArgLeuMETGlyAspLysValSerAlaLysAspAlaMETLysArgAl

1726  CGGCGTCCCCACCGTGCCGGCTCCGACGGCCCGCTGCCGGAAGATGAAGAGAACCGCCCTGGCGATCGC  1794
      aGlyValProThrValProGlySerAspGlyProLeuProGluAspGluThrAlaLeuAlaIleAl
```

FIG. 4C

```
1795  CCGCGGAGGTCGGCTACCCGGTGATCATCAAGGCCGCCGGCGTGGTGGGCGCGGTGGGCGCGGTGGT  1863
      aArgGluValGlyTyrProValIleIleLysAlaAlaGlyGlyGlyGlyArgGlyMETArgValVa

1864  CTACGACGAGTCCGAGCTGATCAAGTCGGCCAAGCTGGCCAAGTCGACCCGACCCGAAGTCGGCGCGGTCGGCAA  1932
      lTyrAspGluSerGluLeuIleLysSerAlaLysLeuThrArgThrGluAlaGlyAlaAlaPheGlyAs

1933  CCCGATGGTCTACCTGGAGAAGTTCCTGACCAACCCGCGCCACGTGGAAGTCCAGTGCTTTCCGACGG  2001
      nProMETValTyrLeuGluLysPheLeuThrAsnProArgHisValGluValGlnValLeuSerAspGl

2002  CCAGGGCAACGCCATCCACCTCGGCGACCGGGCTGCTCCCTGCAGCCGCCACCAGAAGGTGATCGA  2070
      yGlnGlyAsnAlaIleHisLeuGlyAspArgAspCysSerLeuGlnArgArgHisGlnLysValIleGl

2071  AGAGGCGCCGGCCCCCGGCGCATGCGACGAGAAGGCTGCCAGGAAGTCTTCGCCCGTGCCTCCAGGCCTG  2139
      uGluAlaProAlaProGlyIleAspGluLysAlaArgGlnValPheAlaArgCysValGlnAlaCy

2140  CATCGAGATCGGCTACCCGGCGGCCTACTCGGAGTTCCTCTACGAGAACGGCCGCTTCTACTTCAT  2208
      sIleGluIleGlyTyrArgGlyAlaGlyThrPheGluPheLeuTyrGluAsnGlyArgPheTyrPheIl

2209  CGAGATGAACACTCGCGTGCAGGTGGAGCACCCGGTATCTGAGATGGTCACCGGTGTCGACATCGTCAA  2277
      eGluMETAsnThrArgValGlnValGluHisProValSerGluMETValThrGlyValAspIleValLy
```

FIG. 4D

```
2278  GGAGATGCTGCTGCGCATCGCCTCCGGGCGAGAAGCTCTCGATCCGCCAGGAGGACGTGGTCATCCGCGGCCA  2346
      sGluMETLeuArgIleAlaSerGlyGluLysLeuSerIleArgGlnGluAspValValIleArgGlyHi

2347  TGCGCTGGAATGCCGGGATCAACGCCCGAAGACCCTTCATGCCAACGCCTTCATGCCAACGCCCGAAGGTCAAGCA  2415
      sAlaLeuGluCysArgIleAsnAlaGluAspProLysThrPheMETProSerProGlyLysValLysHi

2416  CTTCCACGCCCCCCCGGGCAACGGCGCTACAGCGGCTACAGCGTGCCGCC  2484
      sPheHisAlaProGlyGlyAsnGlyAlaArgValAspSerHisLeuTyrSerGlyTyrSerValProPr

2485  GAACTACGACTCGCTGGTCGGCAAGGTCATCACCTACGGTGCCGACGAGGCGCTGGCCGCGGAT  2553
      oAsnTyrAspSerLeuValGlyLysValIleThrTyrGlyAlaAspArgAspGluAlaLeuAlaArgME

2554  GCGCAATGCCCTGGACGAGTTGATCGTCGACGGTATCAAGACCAATACCGAACTGCACAAGGACCTGGT  2622
      TArgAsnAlaLeuAspGluLeuIleValAspGlyIleLysThrAsnThrGluLeuHisLysAspLeuVa

2623  GCGCGACGCCGCCTTCTGCAAGGGCGTGAACATCCATTACCTGGAGAAGAAACTGGGTATGGACAA  2691
      lArgAspAlaAlaPheCysLysGlyValAsnIleHisTyrLeuGluLysLysLeuGlyMETAspLy

2692  GCACTGATCCGTCAGTCGCTGCGCACAAGGGCTGCCTCCGGGCGGCCCCTTGTCGTTCCGCCTGCCGGC  2760
      sHis.
```

FIG. 4E

```
2761 CGCCCCAACGGTGCTATCCTCGTCGCCCCTCCACCAACCGGACTCCTGCATGGAACGCATCCGCGCTGG 2829
2830 TACCGCCAATCGCTGGCCGCCGGCGACCCGAGGCCGACCTGCTTCGCCCTGGGTTTCAGGGAAAGCCTG 2898
2899 CAACCCGCCGCACTCTTCCGCTCCGCGAGCCTGTGCATTCTCGTCAGCGTGTCTGTGCACCTGGCTGTTC 2967
2968 GTGCATTTCTTCGAACCGATCATCCGCCTCTGCGGCTGGGCCGCTGTACACGGCATTCAGCGTGGCC 3036
3037 AACTTCGCCCTGATCCCCAGCGGCTCGCTGATCGAGGCCGGCCAGCGGTGGCCCGTACTTCGATCCGCTG 3105
3106 GCGGCCTTCAACGGCCTGGCGGGGACTGGCGCAACTGGCGTTCTATTTCGTCGGCTATGCCGCTGTTC 3174
3175 TTCGTCGCCCTGTACGCCGCCAGCATCGTCTTCGGCATCCGCCTGGGCCTGCGCATC 3231
```

FIG. 4F

METHODS AND COMPOSITIONS FOR MODULATING LIPID CONTENT OF PLANT TISSUES

INTRODUCTION

1. Field of the Invention

This invention relates to modulating levels of enzymes and/or enzyme components capable of increasing the amount of malonyl-CoA in plant cells.

2. Background

It is of value in some oilseed crops to increase the lipid content in seed. One means to do so is to increase the rate of fatty acid biosynthesis during storage lipid deposition by some application of genetic engineering technology. However, an exact approach has not been defined or demonstrated even though there have been many possibilities proposed.

Malonyl-CoA is an essential metabolite for several biosynthetic pathways in plants. One pathway for its formation is through the action of acetyl-CoA carboxylase (ACC) (EC 6.4.1.2) on acetyl-CoA and bicarbonate: ACC catalyzes the ATP-dependent carboxylation of acetyl-CoA to malonyl-CoA. In plants, malonyl-CoA is a common intermediate in fatty acid biosynthesis and in the pathway leading to the biosynthesis of cuticular waxes, flavonoids, anthroquinones, N-malonyl-ACC and malonic acid.

In yeast and animal cells, ACC has a rate-limiting role in fatty acid biosynthesis. ACC has been hypothesized to be the rate-limiting step for fatty acid biosynthesis in plants. It therefore is of interest to evaluate the role of ACC carboxylase in fatty acid biosynthesis in plants, as a means of developing methods and compositions for altering the lipid content of plant tissues.

Relevant Literature

Verwoert and coworkers (Verwoert et al., (1992) *Dept. of Genetics* 424–427) cloned the *E. coli* fabD gene encoding malonyl-CoA:ACP transacylase (MTA) and modified it for seed-specific expression. They reported high-level, seed-specific expression of MTA in several plants (rape, petunia, and tobacco) but no significant change was observed in the fatty acid composition or content of the seed.

Although ACC has been suggested as a rate-limiting step for fatty acid biosynthesis in developing seed based on data of Turnham and Northcote, (1983) *Biochem. J.* 212:223–229, the evidence is circumstantial. In vivo studies indicate that fatty acid biosynthesis is a highly regulated pathway; fatty acid biosynthesis in leaves is five-fold higher in the light than in the dark Post-Beittenmiller et al., (1991) *J. Biol. Chem.* 266:1858–1865). Analysis of in vivo pools of acyl-ACP intermediates in these leaf tissues indicated that the ACC-catalyzed reaction is far from equilibrium and thus potentially a rate-limiting step in the pathway (Post-Beittenmiller et al., (1991) supra.

ACC enzymes from *E. coli*, from yeast (Al-Feel et al., (1992) *Proc. Natl. Acad. USA* 89:4534–4538), and from animal cells (rat liver) (Lopez-Castillas et al., (1988) *Natl. Acad. Sci. USA* 85:5784–5788) are relatively well characterized; complete primary structures deduced from cloned genes are available. Animal and yeast ACC enzymes have all the functional peptide units of ACC (biotin carboxylase, BC); (carboxyl carrier protein, BCCP); (transcarboxylase, TC) assembled into one comparatively large multifunctional protein encoded by a single gene Al-Feel et al., (1992) *Proc. Natl. Acad. USA* 89:4534–4538;Lopez-Castillas et al., (1988) *Proc. Natl. Acad. Sci. USA* 85:5784–5788 whereas in prokaryotes the function of units of ACC are separate.

The structure of ACC in plants is less clear. ACC enzyme from wheat germ, parsley suspension cultures, and rape seed and leaf is composed of a single high molecular weight polypeptide of approximately 200–240 kDa (e.g., Slabas and Hellyer, (1985) *Plant Sci.* 39:177–182; Slabas et al., (1986) *Soc. Trans. Lond.* 14:716; Egin-Buhler and Ebel, 1983) *Eur. J. Biochem.* 133:335–339). However, Kannangara and Stumpf, (1972) *Archives of Biochem. and Biophys.* 152:83–91 demonstrated that the spinach ACC isolated from disrupted chloroplasts can be resolved in two activities: BC found with BCCP in lamellar fractions, and TC found in the stroma. Whether the enzyme in vivo may actually be a single peptide is still not known. However, a protein fraction containing an *E. coli* TC could replace the TC fraction from spinach chloroplast extracts in an in vitro assay system when combined with the fraction containing plant "BCCP" and plant "biotin carboxylase" (Kannangara and Stumpf, 1972). Moreover, an *E. coli* extract containing BC and BCCP exhibited ACC activity when combined with a plant extract containing TC activity. Although these in vitro data suggest the possibility that an *E. coli* ACC subunit might contribute some functional role to plant ACC in vivo, the experiments did not establish whether plant BC could interact functionally with an *E. coli* BCCP.

SUMMARY OF THE INVENTION

Novel compositions and methods are provided for modifying the malonyl-CoA dependent biosynthetic pathways, particularly to modify lipid levels, in plant tissues of interest. The methods involve transforming a plant cell of interest with an expression cassette functional in a plant cell comprising a transcriptional and translational initiation regulatory region, joined in reading frame 5' to a DNA sequence encoding an ACC component capable of modulating the production of malonyl-CoA, and translational and transcriptional termination regions. Expression of the ACC component provides for an increase in lipid production as a result of altered concentrations of malonyl-CoA for enzymes involved in lipid biosynthesis. Of particular interest is the selective control of lipid production in plant tissues such as leaves, roots, fruits and seeds.

BRIEF DESCRIPTION OF THE DRAWINGS

FIGS. 3A–F (pCGN3916): 3077 bases of *E. coli* strain mm294 chromosome containing the accB and accC genes (SEQ ID NO:01). Translation from bases 800–1267 FIGS. B and C represent the preprotein of BCCP(SEQ ID NO:02); 1281–2627 the BC enzyme (FIGS. B,C and D)(SEQ ID No. 03)

FIGS. 4A–F (pCGN3933): 3231 bases of Pseudomonas aeruginosa strain PaO chromosome, containing the accB and accC genes (SEQ ID NO:04) Translation from bases 861–331 (FIGS A,B and C) represent the preprotein of BCCP (SEQ ID NO:05); 1349–2698 the BC enzyme (FIGS B,C and E) (SEQ ID NO:06)

DESCRIPTION OF THE PREFERRED EMBODIMENTS

Figure 1:
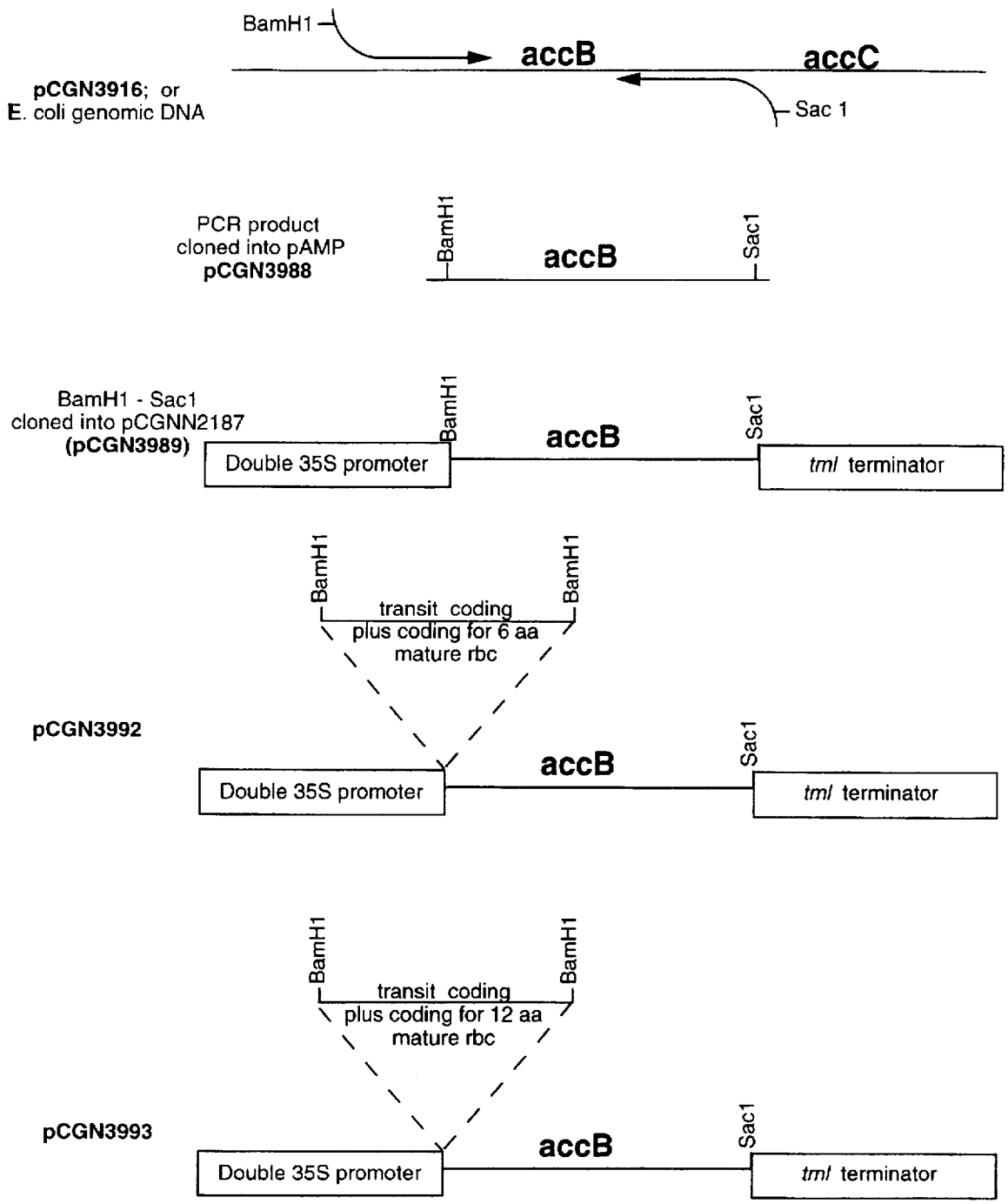
FIG. 1 shows the construction of pCGN3989, pCGN3992, and pCGN3993. The accB coding region was amplified by polymerase chain reaction (PCR) using synthetic DNA primers which place a BamH1 recognition sequence immediately upstream of the accB initial ATG codon and a Sac1 recognition sequence just downstream of the translational stop codon. The accB coding region was then excised from pCGN3988 as a BamH1-Sac1 fragment which was directly subcloned into pCGN2187 to create pCGN3989 (see FIG. 2, pCGN2187). In the case of pCGN3992, a BamH1 fragment was subsequently added to pCGN3989 to create a sequence encoding a fusion protein containing the chloroplast transit region of ribulose bisphosphate carboxylase (RUBISCO) plus the first six amino acids of mature RUBISCO. In the case of pCGN3993, the added BamH1 fragment encoded the complete transit region plus 12 amino terminal amino acid residues of mature RUBISCO.
Figure 2:
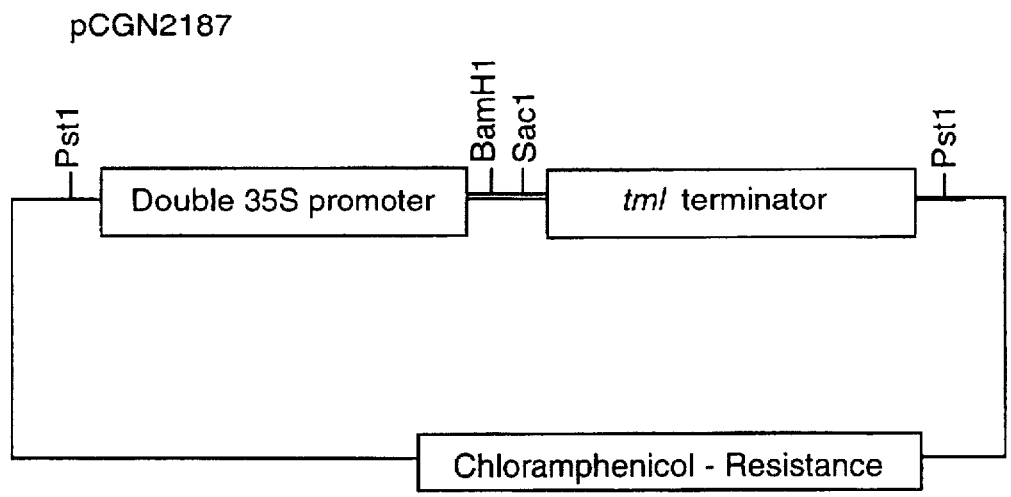
FIG. 2 shows the composition of pCGN2187. The promoter region, entitled double 35S or d35S, contains bases −363 to −90 of the cauliflower mosaic virus (CaMV) genome (Gardner et al., (1981) Nucl. Acids Res. 9:2871–2888) fused to bases −941 to +112 of the CaMV genome. The transcription terminator region is derived from bases 11207 to 10069 of the octopine Ti Plasmid pTiA6 using the numbering system of Barker et al., (1983) Plant Mol. Biol. 2:335–350. The terminator region corresponds to the functional counterpart of a "tml" gene in the Agrobacterium T-DNA and is thus termed tml.

In accordance with the subject invention, novel DNA sequences, DNA constructs, methods and compositions are provided which permit modification of the lipid content of plant products by means of increased production of a substrate for lipid biosynthesis, malonyl-CoA (MCA), in a tissue of interest. Plant cells are transformed with an expression cassette comprising a DNA encoding an ACC polypeptide capable of increasing the amount of malonyl-CoA in the tissue of interest. Desirably, integration constructs may be prepared which provide for integration of the expression cassette into the genome of a plant host. Depending upon the desired application, the ACC polypeptide can be preferentially expressed in a tissue of interest and/or a particular organelle. Tissue specificity is accomplished by the use of transcriptional regulatory regions having the desired expression profile. Translocation of the enzyme to a particular organelle is accomplished by the use of an appropriate translocation peptide.

To provide for an increased level of lipid in a plant, a plant cell is transformed with an expression cassette which includes as operably linked components in the 5'–3' direction of transcription, a transcriptional and translation initiation region, a structural gene encoding an ACC polypeptide capable of increasing levels of malonyl-CoA, and a transcriptional and translational termination regulatory region. For organelle targeting, a DNA sequence encoding a transit peptide and processing signal is included. Expression in plant tissue cytoplasm may be sufficient to modulate lipid biosynthesis pathways found outside of plastid organelles. The initiation and termination regulatory regions are functional in the host plant cell and may be either homologous or heterologous to the host plant and to the structural gene.

Of particular interest as a means of increasing malonyl-CoA concentration is use of an ACC polypeptide which is capable of metabolizing malonyl-CoA from substrates normally found in plant cell. Particularly of interest is an ACC polypeptide which acts on the malonyl-CoA precursors for the desired end use. By ACC polypeptide is intended a polypeptide which contributes to the conversion of acetyl-CoA to malonyl-CoA. By polypeptide is meant any chain of amino acids, regardless of length or post-translational modification (e.g. glycosylation or phosphorylation). The polypeptide may be a component subunit of ACC carboxylase, for example BCCP, TC, or BC, or any combination of subunits, including the entire carboxylase enzyme. The polypeptide can also be any portion of a subunit alone or in combination with other subunits.

Considerations for use of a specific ACC polypeptide in plant tissue for the production of precursors of malonyl-CoA biosynthesis include pH optimum of the polypeptide, whether the ACC polypeptide is a rate-limiting enzyme or a component thereof, i.e., the product of the enzyme used is essential for fatty acid biosynthesis, and co-factors required by the polypeptide. The ACC polypeptide should have kinetic parameters compatible with the biochemical environment found in the host plant cell. For example, the polypeptide may have to compete for substrate with other enzymes. Analysis of the $K_m$ and specific activity of the polypeptide in question therefore should be considered in determining the suitability of a given polypeptide for increasing malonyl-CoA production in a given host plant. The polypeptide thus is one which can function under conditions present in the desired target tissue, but otherwise can be any ACC polypeptide having the desired characteristic of being capable of positively increasing the production of malonyl-CoA. Of interest as a source of an ACC polypeptide is a component of an enzyme which produces MCA, particularly *E. coli* ACC.

The *E. coli* ACC enzyme can be separated into four subunits: biotin carboxyl carrier protein (BCCP), a dimer of two 22.5 kDa subunits, biotin carboxylase (BC), composed of two 51 kDa subunits, and transcarboxylase (TC), composed of two 30 kDa subunits and two 35 kDa subunits (Alberts and Vagelos, (1972) p. 37–82. In P. D. Boyer (ed), The Enzymes, 3rd ed., Vol. 6. *Academic Press*, New York). The four genes that specify the individual subunits of the *E. coli* enzyme have been cloned and their nucleic acid sequences have been determined: accB(fabE) Muramatsu and Mizuno, (1989) *Nucleic Acids Res.* 17:3982 and accC (fabg) Kondo et al., (1991) *Proc. Natl. Acad. Sci. USA* 88:9730–9733 encode the BCCP and BC subunits respectively, and accA and accD (dedB) encode the αand βsubunit of the TC protein (Li and Cronan, (1992) *J. Biol. Chem.* 267:16841–16847). These genes can be individually expressed in transgenic plants to effect greater synthesis of MCA.

Other sources of ACC subunits substantially identical to the *E. coli* subunits also can be used.

By "substantially identical" is meant an amino acid or nucleic acid sequence exhibiting at least 60%, preferably 80%, more preferably 90%, and most preferably 95% homology to a reference amino acid or nucleic acid sequence. For polypeptides, the length of comparison sequences will generally be at least 16 amino acids, preferably at least 20 amino acids, or preferably at least 25 amino acids, and most preferably 35 amino acids. For nucleic acids, the length of comparison sequences generally will be at least 50 nucleotides, preferably at least 60 nucleotides, more preferably at least 75 nucleotides, and most preferably 110 nucleotides. Homology typically is measured using sequence analysis software (for example, sequence analysis software package of the Genetics Computer Group, University of Wisconsin Biotechnology Center, 1710 University Avenue, Madison Wis. 53705). Such software matches similar sequences by assigning degrees of homology to various substitutions, deletions and other modifications. Conservative substitutions typically include substitutions within the following groups: glycine and alanine; valine, isoleucine and leucine; aspartic acid and glutamic acid, asparagine and glutamine; serine and threonine; lysine and arginine; and phenylalanine and tyrosine.

For the most part, some or all of the coding sequence for the ACC polypeptide will be from a natural source, and the structural gene which is a source for DNA encoding the ACC polypeptide can be obtained in a variety of ways. It can be obtained from various prokaryotic cells as well as from various eukaryotic cells: both eukaryotic and prokaryotic cells are capable of producing MCA. ACC polypeptide is obtainable from *E. coli* and from other prokaryotic ACC enzymes such as *Pseudomas aeruginosa* ACC enzyme and *Bacillus subtilis* ACC enzyme. Plant chloroplast ACC may consist of discrete subunits such as are found in *E. coli*, and thus resemble a prokaryotic enzyme structure. Plant chloroplast ACC therefore may also be a source of ACC polypeptide. For example, several diverse plants contain within their chloroplastic genomes certain DNA sequences, exemplified by the pea zpfA, which possibly encode proteins sharing homology with the βsubunit of the *E. coli* TC protein (Li and Cronan, (1992) *Plant Molec. Biol.* 20:759–761).

In some situations it may be desirable to modify all or a portion of the codons, for example to enhance expression, by employing host-preferred codons. Methods for identifying sequences of interest have found extensive exemplication in the literature, although in individual situations, different degrees of difficulty may be encountered. Various techniques include the use of probes where genomic or cDNA libraries may be searched for complementary sequences. The coding sequence for the ACC polypeptide may be synthesized in whole or in part, particularly where it is desirable to provide plant preferred codons. Thus, all or a portion of the open reading frame may be synthesized using codons preferred by the plant host. Plant preferred codons may be determined from the codons of highest frequency in the proteins expressed in the largest amount in the particular plant species of interest. Methods for synthesizing sequences and bringing the sequences together are well established in the literature.

Where a portion of the open reading frame is synthesized, and a portion is derived from natural sources, the synthesized portion may serve as a bridge between two naturally occurring portions, or may provide a 3'-terminus or a 5'-terminus. Particularly where a leader sequence is used and the open reading frame encoding the ACC polypeptide and the leader sequence are derived from different genes, synthetic adapters commonly will be employed. In other instances, polylinkers can be employed, where the various fragments can be inserted at different restriction sites or substituted for a sequence in the polylinker.

In vitro mutagenesis and selection, site-directed mutagenesis, or other means may be employed to obtain mutations of naturally occurring ACC genes to produce an ACC polypeptide with activity in vivo with more desirable physical and kinetic parameters for function in the plant cell, such as a higher rate of production of MCA.

If the ACC polypeptide coding sequence is from a prokaryotic source, in order to have expression of the gene in a plant cell, transcriptional and translational initiation regulatory regions or promoters functional in plant cells must be provided operably linked to the coding sequence. Transcription and translation initiation signals functional in plant cells include those from genes which are present in the plant host or other plant species, and direct a fairly uniform or constitutive expression in a plant host, for example those present in viruses such as the cauliflower mosaic virus (CaMV), for example the 35S transcriptional initiation region and those associated with T-DNA such as the opine synthase transcriptional initiation regions, for example, octopine, mannopine, agropine, etc. The transcription and translation initiation regions may be obtained from the same or different 5' non-coding upstream regulatory region(s). Of particular interest is a transcriptional initiation region in a construct comprising two 35S promoters in tandem (also referred to as a "Double 35S" promoter), mannopine synthase/35S promoter constructs (See, U.S. Pat. No. 5,106, 739 issued Apr. 21, 1992 and Comai, et al., *Plant Mol. Biol.*, (1990) 15:373–381), 34S promoters (See, 404,283 filed Sept. 7, 1989 and Sanger, et al., *Plant Mol. Bio.*, (1990) 14:433–443).

By "promoter" is intended a sequence sufficient to direct transcription. Also included are those promoter elements which are sufficient to render tissue specific gene expression; such elements may be located in the 5' or 3' regions of a native gene. By "operably linked" is meant that a gene and a regulatory sequence(s) are connected in such a way so as to permit gene expression when the appropriate molecules (for example, transcriptional activator proteins) are bound to the regulatory sequence(s). By "plant cell" is meant any self-propagating cell bounded by a semi-permeable membrane and containing a plastid. Such a cell also requires a cell wall if further propagation is desired. Plant cell, as used herein, includes without limitation, seeds, suspension cultures, embryos, meristematic regions, callous tissue, leaves, roots, shoots, gametophytes, sporophytes, pollen, and microspores.

Depending upon the application, promoters also may be obtained from genomic clones of cDNAs which demonstrate preferential expression according to a specific tissue and/or timing profile. For example, leaf specific cDNAs (Dunsmuir, et al. *Nucleic Acids Res.* (1983) 11:4177–4183), root tips (Pokalsky, et al. *Nucleic Acids Res.*, (1989) 17:4661–4673), and fruit (Peat et al. *Plant Mol. Biol.*, (1989) 13:639–651) and the like can be employed. Within such classes of promoters, further differentiation may be observed between more generalized tissue specific promoters and very localized or timing specific promoters. For example, promoters showing differential expression patterns in fruit are described in U.S. Pat. No. 4,943,674, issued Jul. 24, 1990 and in co-pending applications U.S. Ser. No. 582,241, filed Sept. 14, 1990 (also WO-A 8 809 334), U.S. Pat. No. 5,175,095 issued Dec. 29, 1992 (also EP-A 0 409 629), and U.S. Ser. No. 555,711, filed Jul. 19, 1990 (also EP-A 0 409 625). Depending upon the specific application, a promoter is chosen which provides the desired expression pattern. Promoters demonstrating preferential transcriptional activity in plant tissues are described in U.S. Ser. No. 742, 834, filed Aug. 8, 1991 (also EP-A 0 255 378) and U.S. Ser. No. 494, 722 (also WO-A 9 113,980). Other promoters from genes which have a differential pattern of expression in a specific tissue can be identified by differential screening of a tissue of interest, using methods described for example in U.S. Pat. No. 4,943,674 and EP-A 0255378.

The regulatory regions may be homologous (derived from the plant host species) or heterologous (derived from source foreign to the plant host species), to the plant host or a synthetic DNA sequence. The term "homologous" includes both indigenous and endogenous sequences. In order to join the promoter(s) to the structural gene, the non-coding 5' region upstream from the structural gene may be removed by endonuclease restriction. Alternatively, where a convenient restriction site is present near the 5' terminus of the structural gene, the gene can be restricted and an adapter employed for linking the structural gene to a promoter region, where the adapter provides for any lost nucleotides of the structural gene.

The termination region can be derived from the 3'-region of the gene from which the initiation region was obtained or from a different gene. The termination region can be derived from a plant gene, particularly from the same plant gene used as a source of sequences to initiate transcription and translation. Other 3'-regions include the tobacco ribulose bisphosphate carboxylase small subunit termination region; a gene associated with the Ti-plasmid such as the octopine synthase termination region; the tml termination region; and other 3'-regions known to those skilled in the art.

Various components of fatty acid synthesis are located in the chloroplast and/or proplastid organelles. Therefore, it is desirable that the ACC polypeptide be translocated to the specific organelle. Accordingly, DNA coding for a translocation or transit peptide optionally including a processing signal, recognized by the plant host can be included in the construct. The transit peptide, also known as a leader sequence, and processing signal may be derived from gene encoding any plant protein which is expressed in the cytoplasm and translocated to the appropriate organelle. For some applications, the leader sequence can be combined in a DNA construct with a seed specific promoter, for example to increase expression in a target tissue of interest, and for others, the leader sequence can be provided under the regulatory control of a more constitutive transcriptional initiation region. By "transit peptide" is meant a sequence capable of translocating a peptide joined to the transit peptide to a particular organelle. For the most part, the transit peptide is from one plant, but is generally recognized by other plants. Thus, the DNA encoding the transit peptide may be native to or heterologous to the ultimate host in which the chimeric gene is introduced. DNA encoding transit peptides may come from soybean, corn, petunias, tobacco, Brassica, tomato, wheat, pea and the like.

The DNA encoding the transit peptide may be the complete transit peptide encoding sequence including the processing signal or a truncated transit-peptide-encoding sequence lacking from about 1 to 10 codons, or a portion of a codon, from the 3' terminus. In addition, one or more changes may be made in the nature of mutations, deletions or insertion in the transit peptide and processing signal, where such change may provide for convenience in construction by providing for a convenient restriction site, or removing an inconvenient restriction site. The mutations may be conservative or non-conservative, so that the transit peptide may be the same or different from the wild-type transit peptide. An additional peptide segment between the transit peptide and the ACC polypeptide may be useful. Such peptide may be the mature (post-processing) amino-terminal portion of the structural peptide or any other peptide providing the appropriate structure features recognized and needed by the plastid translocation system. When post processing amino acids from the SSU leader sequence are included, it is preferred that no more than 50, preferably no more than 40, and most preferably no more than 30 post processing amino acids are present at the N-terminal of the desired ACC polypeptide. However, use of a seed-specific promoter may be desired to selectively modify Since seed differs from leaf tissue, it may be necessary to use different lengths of RUBISCO mature sequence with the transit sequences, or a different transit sequence altogether may be necessary for greatest benefit. In this regard, it is important to note that gene constructs lacking DNA encoding a transit sequence for organelle targeting also may have value since the ACC enzyme product (malonyl-CoA) also is used in extension of 18-carbon fatty acids into longer molecules in plants such as rapeseed and meadowfoam. These extension reactions take place in the cytoplasm, so targeting to the chloroplast or proplastid organelles is not necessary for such applications. However, use of a seed-specific promoter may be desired to selectively modify malonyl-CoA levels in the plant.

In developing the expression cassette, the various fragments comprising the regulatory regions and open reading frame may be subjected to different processing conditions, such as ligation, restriction enzyme digestion, resection, in vitro mutagenesis, primer repair, use of linkers and adapters, and the like. Thus, nucleotide transitions, transversions, insertions, deletions, or the like, may be performed on the DNA which is employed in the regulatory regions and/or open reading frame. The expression cassette thus may be wholly or partially derived from natural sources, and either wholly or partially derived from sources endogenous to the host cell, or exogenous to the host cell. Furthermore, the various DNA constructs (DNA sequences, vectors, plasmids, expression cassettes) of the invention are isolated and/or purified, or synthesized and thus are not "naturally occurring."

During the construction of the expression cassette, the various fragments of the DNA usually will be cloned in an appropriate cloning vector, which allows for amplification of the DNA, modification of the DNA or manipulation by joining or removing of sequences, linkers, or the like. Normally, the vectors will be capable of replication in at least a relatively high copy number in *E. coli*.

A number of vectors are readily available for cloning, including such vectors as pBR322, pUC series, M13 series, etc. The cloning vector will have one or more markers which provide for selection of transformants. The markers will normally provide for resistance to cytotoxic agents such as antibiotics, heavy metals, toxins, or the like. Often times, markers are selected which can be detected in a plant host. Where the DNA will be microinjected or propelled into the plant cell, a marker usually is chosen which allows for direct selection of those cells in which the injected DNA has become integrated and functional. By appropriate restriction of the vector and cassette, and as appropriate, modification of the ends, by chewing back or filling in overhangs, to provide for blunt ends by addition of linkers, by tailing, complementary ends can be provided for ligation and joining of the vector to the expression cassette or component thereof.

After each manipulation of the DNA in the development of the cassette, the plasmid will be cloned and isolated and, as required, the particular cassette component analyzed as to its sequence to ensure that the proper sequence has been obtained. Depending upon the nature of the manipulation, the desired sequence may be excised from the plasmid and introduced into a different vector or the plasmid may be restricted and the expression cassette component manipulated, as appropriate. The manner of transformation of a prokaryotic cloning host with the various DNA constructs (plasmids and viruses) for cloning is not critical to this invention. Commonly, the expression cassette will be joined to a replication system functional in prokaryotes, particularly *E. coli*, so as to allow for cloning of the expression cassette for isolation, sequencing, analysis, and the like. In most cases the DNA construct will include one or more markers which may allow for selection in the host(s), the markers usually involving biocide resistance, for example antibiotic resistance; heavy metal resistance; toxin resistance; complementation, providing prototropy to an auxotrophic host; immunity; etc. Conjugation, transduction, transfection or transformation, for example, calcium chloride or phosphate mediated transformation, also may be employed.

Depending upon the manner of introduction of the expression construct into the plant, other DNA sequences may be required. As discussed above, various marker sequences may find application. In addition, sequences useful to transformation also may be included. For example, the use of T-DNA for transformation of plant cells has received extensive study and is amply described in Hoekema, *The Binary Plant Vector Systems*, Offsetdrukkerij Kanters B. V., Alblasserdam, 1985, Chapter V. Knauf et al., "Genetic Analysis of Host Range Expression by Agrobacterium." In: *Molecular Genetics of the Bacteria-Plant Interaction*, Puhler, A. ed., Springer-Verlag, N.Y., 1983, p. 245, and An et al., *EMBO J.*, (1985) 4:277–284. Conveniently, explants, cotyledons, or other plant tissue may be cultivated with *A. tumefaciens* or *A. rhizogenes* to allow for transfer of the expression construct to the plant cells, the plant cells dispersed in an appropriate selective medium for selection, grown to callus, shoots grown and plantlets regenerated from the callus by growing in rooting medium. The Agrobacterium host will contain a plasmid having the vir genes necessary for transfer of the T-DNA to the plant cells and may or may not have T-DNA. If the expression construct is to be inserted into the host cell by injection or electroporation, disarmed Ti-plasmids (lacking the tumor genes, particularly the T-DNA region) may be used.

Examples of suitable plant hosts include soybean, sunflower, corn, peanut, maize, cotton, safflower and rapeseed. Other plant hosts which may be used include tomato, strawberries, melons, banana, ornamental plants and the like. Various techniques exist for determining whether the desired DNA sequences present in the plant cell are integrated into the genome and are being transcribed. Techniques such as the Northern blot can be employed for detecting messenger RNA which codes for the ACC polypeptide. In addition, the presence of expression can be detected in a variety of ways, such as assaying for enzyme activity or immunoassay for the protein product. A desired phenotype in this case is increased lipid content in a plant tissue of interest, particularly leaves and seed.

By "transformed cell" or "transgenic cell" is meant a cell into which (or an ancestor of said cell) into which by means of recombinant DNA techniques, DNA encoding an ACC polypeptide has been introduced. Plant cells transformed with a plant expression vector can be regenerated, for example, from single cells, callous tissue or leaf disks according to standard plant tissue culture techniques.

Transgenic plants expressing a selectable marker, are screened for transmission of the transgene DNA by standard DNA detection techniques. Each positive transgenic plant and its transgenic progeny are unique in comparison to other transgenic plants established with the same transgene. Integration of the transgene DNA into the plant genomic DNA is in most cases random and the site of integration can profoundly affect the levels, and the tissue and development or patterns of transgene expression. Consequently, a number of transgenic lines are usually screened for each transgene to identify and select plants with the most appropriate expression profiles.

The cells which have been transformed may be grown into plants in accordance with conventional ways. See, for example, McCormick et al., *Plant Cell Reports* (1985) 5:81–84. These plants may then be grown, and either self pollinated or cross-pollinated identifying the resulting hybrid having the desired phenotypic characteristic. Two or more generations may be grown to ensure that the subject phenotypic characteristic is stably maintained and inherited and then seeds harvested for use to provide plants having the new phenotypic property expressed in a desired plant tissue, particularly increased lipid levels due to production of lipid synthesis precursors.

The subject invention finds use in increasing the level of malonyl-CoA present in a plant cell. Malonyl-CoA is involved in several different plant biosynthetic pathways, therefore an increase of malonyl-CoA levels has a variety of applications. For example, increased malonyl-CoA in leaf tissue increases the lipid content, increased malonyl-CoA in seed tissue may also increase lipid content in such tissues; increased malonyl-CoA in plant fruit tissue (e.g., tomato fruit, cotton ball, rapeseed pod) hastens and/or facilitates fruit abscission by increasing ethylene production; increased malonyl-CoA in the tissues which are capable of producing flavonoids or cuticular waxes results in increased production of these components, leading to modified flavor or increased drought tolerances, respectively.

Additionally, BCCP can function as a non-specific $CO_2$ donor in the plant cell, thus overexpression of the BCCP subunit provides a method for increasing activity of other biotin-containing carboxylases, e.g. 3-methylcrotonylCoA carboxylase (involved in catabolism of leucine), propionyl-CoA carboxylase (involved in degradation of branched-chain amino acids and odd numbered fatty acids), and pyruvate carboxylase (for gluconeogenesis and lipogenesis).

The following examples are offered by way of illustration and not by limitation.

EXAMPLES

Example 1

Construction of BCCP gene constructs for expression in leaves.

Plasmids pCGN3994, pCGN3995, and pCGN3996 contain the complete coding sequence for the 156 amino acid *E. coli* BCCP gene, a CaMV 35S promoter, tml 3' transcription termination sequence from the Agrobacterium Ti plasmid for plant expression, and a kanamycin (npt) resistance gene for selection in plants. All three plasmids are derived from pCGN3988, which contains the *E. coli* accB gene. pCGN3988 is prepared as follows, using the polymerase chain reaction (PCR). The template for the PCR chain reaction is pCGN3916, a Bluescript KS+ plasmid (Stratagene Cloning Systems, La Jolla, Cali. ) containing an approximately 6.5 kb fragment of the *E. coli* MM294 (ATCC #33625) chromosome that includes accB and flanking sequences. The PCR reaction as described can be performed using *E. coli* MM294 genomic DNA as a template rather than pCGN3916. Genomic DNA from *E. coli* MM294 is isolated as described by Silhavy and Coworkers (Silhavy, et al., (1984) Experiments with Gene Fusions, Cold Spring Harbor, N.Y. ). The complete coding sequence of the *E. coli* accB contained on pCGN3916 is shown in FIG. 3, and is available in GENBANK under the acquisition number M83198. The forward and reverse primers for amplification included restriction endonuclease cleavage sites for BamHI and SacI respectively, and have the following sequences:

5'-CUACUACUACUAGGGGATCCTATGGATATCGT AAGATT-3'(SEQ ID NO: 07) (forward primer), and 5'-CAUCAUCAUCAUGAGCTCTTACTCGATGACG ACCAG-3'(SEQ ID NO:08) (reverse primer). PCR reactions were performed using a GeneAmp Kit (Perkin-Elmer Cetus, Norwalk, Conn. ) and a programmable thermocycler (Perkin-Elmer Cetus). Amplification was as follows: 15 cycles of 94° C. for 1 min, 55° C. for 2 min, 72° C. for 3 min., 10 cycles of 1 min 94° C., 2 min. at 55° C., and 72° C. for 3 min. 15 sec.

initially and increasing the time by 15 seconds each cycles such that the last cycle is 5 min. 45 sec. Reactions were performed in a 100 µl volume and contained 100 ng supercoiled plasmid DNA as template, 1 µM forward and reverse primer, 0.2 mM of each of the four deoxyribonucleoside triphosphates (dNTP), 50 mM KCl, 10 mM Tris-HCl (pH 8.3), 1.5 mM $MgCl_2$, 0.01% gleatin, and 2.5 units of Taq DNA polymerase. The amplified product was cloned into pAMP1 using the BRL CloneAmp system (BRL, Gaithersburg, Md) and conditions recommended by the supplier. One clone, the sequence of which was verified as having an exact match with the *E. coli* accB sequence (Muramatsu and Mizuno, (1989) *Nucleic Acids Research* 17:3982), was named pCGN3988.

Transcriptional regulatory sequences for expression in plants were attached to the *E. coli* accB in the following manner. The approximately 500 bp BamHI-SacI insert in pCGN3988 was inserted into similarly cleaved pCGN2187 (see FIG. 1) plasmid DNA. In the resulting plasmid, pCGN3989, accB is transcribed from the CaMV d35S promoter and transcription terminates in the tml 3' sequence downstream of accB.

Additional plant sequences were added to plasmid pCGN3989 to direct the *E. coli* BCCP to the chloroplast/plastid. Relatively few data are available concerning the optimal amount of targeting sequence necessary for chloroplast/plastid localization. It therefore was necessary to determine this empirically, and constructs were designed that would allow the addition of the transit peptide (TP) from the small subunit of ribulose bisphosphate carboxylase (RUBISCO) from soybean, required for plastid localization, and DNA sequences encoding either 6 or 12 amino terminal amino acids of the mature small subunit (SSU) gene from the pea RUBISCO. Two cloning steps were required. First, XbaI-SalI fragments from Bal31 digested derivatives of pCGN1096, pCGN1113 and pCGN1119, containing the TP and 6 or 12 amino acids of the mature SSU respectively, were cloned into pCGN566.

pCGN566 was prepared as follows. pUC12 ($Cm^R$ and pUC13 ($Cm^R$) (Ken Buckley Ph.D. thesis, U.C. San Diego) were each digested with EcoRI and HindIII and polylinkers from pUC18 and pUC19 were inserted respectively into the linearized pUC12 and pUC13 to give pCGN565 and pCGN566 respectively. Each of the plasmids carry a chloramphenicol resistance marker.

pPMG 11 (Comai et al., (1983) *Science* 221:370) contains a mutated aroA gene resistant to glyphosate inhibition as a SalI-HindIII fragment. pPMG was digested with SalI and BgII and inserted into BamHI-SalI digested pACYC184 (Chang and Cohen, (1978) *J. Bacteriol.* 134:1141) to provide pPMG17, with the aroA fragment. pUC9 (Vieira and Messing, (1982) *Molecular Cloning* Cold Spring Harbor Lab Manual) was partially digested with AccI and pPMG17 partially digested with HpaII to provide an about 1.6 kbp fragment which was inserted into the AccI site of pUC9 to provide pPMG31. pPMG31 was digested with HindIII, resected about 150 bp with Bal31, BamHI linkers ligated to the linear DNA and the DNA digested with BamHI and SalI. The resulting fragment carried the aroA gene with 8 bp of the 5' untranslated region (TGAGTTTC-sense strand). The fragment was inserted into M13mp9 (Messing and Vieira, (1982) *Gene* 19:269) which had been digested with BamHI and SalI to yield the phage M-13-65B48 containing the aroA gene as a BamHI-SalI fragment.

M-13-65B48 was digested with NarI and PstI, generating an aroA fragment lacking the DNA region 5' of the NarI site, corresponding to the amino terminal portion of the gene. This fragment was cloned in pUC8 cut with AccI and PstI, resulting in pPMG58. This plasmid encodes a lac-aroA fusion protein in which 11 amino acids of the pUC8 lac alpha gene replace the 14 amino acids of he N-terminus of the aroA gene. pPMG34 has been described previously (Stalker et al., (1985) *J. BioL Chem.* 260:4724–4728). The BamHI to SalI fragment containing the aroA gene was cloned in pUC9, resulting in pPMG34.1. Starting from the BanHI site, the 5'-untranslated region of the aroA gene was recessed by treatments with T4 DNA polymerase in the presence of a single nucleoside triphosphate, followed by mung bean nuclease digestion. After each T4 DNA Polymerase and mung bean treatment, the fragment was subcloned as a blunt to SalI insert into a pUC vector, and transformants were screened for the expected product. After two of these steps a clone into a pUC18 was isolated in which the first nucleotide of the Met codon was part of an XbaI site (... tctagatg). This plasmid, called pPMG34.2, was cut with XbaI, treated with T4 polymerase in the presence of dGTP, followed by mung bean nuclease, and T4 DNA ligase. The DNA was transformed into *E. coli* LC3, an aroA mutant, (Comai et al., (1983) *Nature* 317:741–744) and transformants were selected on minimal medium. Several plasmids complementing the aroA phenotype were characterized. Plasmid pPMG34.3 was found to carry an aroAIlac fusion in which the first nucleotide of the aroA Met codon had been deleted.

M-13-65B48 was digested with BamHI and SalI and the resulting BamHI-SalI fragment inserted into the BamHI-SalI site of pCGN565. The resulting plasmid, pPMG63, was first linearized with XmaI, followed by digestion with mung bean nuclease to remove the overhangs, and the resulting fragment ligated to SphI linkers, followed by digestion with SphI and SalI.

pCGN566 was completely digested at the unique SphI and SalI sites and the SphI-SalI fragment containing the aroA gene inserted into the site to provide pPMG64 which contains the chloramphenicol resistance gene.

pPMG64 was digested with SphI and a 0.6 kb pCGN330 SphI fragment inserted into the SphI site so as to provide the RUBPCssu leader peptide in the proper orientation with the aroA gene. The SphI site is proximal to the 3'-terminus of exon 1 of the RUBPCssu gene. The SphI and BamHI sequences are separated by a single base pair and provide for the RUBPCssu leader peptide and processing signal in proper reading frame with the aroA gene. The sequence is as follows:

... ACAAT | GCATGC | C | GGATCC | CG | TGACTTTC | ATGGAA (SEQ ID NO:09) ...

| RUBPCss coding region | SphI | linker region | BamHI | 5'-UT aroA region | aroA coding region |

The resulting plasmid pPMG70 was digested with HindIII to remove the upstream untranslated (UT) region of the small subunit to provide plasmid pPMG72. Plasmid pPMG72 was treated with HindIII and EcoRI, and the SSUaroA promoter/gene fragment was cloned in pSP64 (Melton et al., (1986) *Nucleic Acid Research* 12:7035) which had been digested with HindIII and EcoRI providing plasmid pCGN1068. The vector pSP64 allows in vitro transcription of cloned DNA.

This fusion was planned in such a way that 24 amino acids of the mature SSU peptide are present between the small subunit transit peptide and the aroA sequence. Plasmid pCGN1068 was cut with XbaI, the resulting stoppered ends were "filled" with the large EcoRi DNA polymerase fragment (Klenow fragment), the plasmid was cut again with SmaI and ligated. This caused the loss of a BamHI site present between the XboI and SmaI site. The resulting plasmid pCGN1075 was cut with EcoRI and HindIII releasing the SSU-aroA chimeric gene (Fusion 1). This gene was cloned in Bluescribe-M13 vector (Vector Cloning Systems, San Diego) cut with EcoRi and Hindlll resulting in pCGN1076. Plasmid pCGN1076 was cut with SphI and BamHI and a 70 bp SphI-Seu3A fragment from a pea SSU cDNA clone was ligated to pCGN1076 resulting in pCGN1077. Such 70bp SphI-Seu3A fragment was isolated by digesting plasmid pSS15 (G. Corussi et al., (1983) *J. Biol. Chem.* 258:1399) with Seu3A and SphI, separating the resulting fragments by agarose gel electrophoresis and electroelution from the gel. The chimeric gene in pCGN1077 consisted of the transit peptide of the soybean SSU, part of the mature pea SSU (24 amino acids) and the aroA gene.

The following is the construction scheme: the aroA moiety of pCGN1077 was removed by digestion with SphI and SalI. In its place was cloned the region coding for the mature SSU, as an SphI and PstI, and then excising it with SphI and SalI. The resulting plasmid, pCGN1094, codes for an hybrid SSU having the transit peptide of the soybean clone, and the mature portion of the pea clone and carries SstI and EcoRI sites 3' of this coding region. The HindIII to BamHI region of transposon Tn5 (Jorgensen et al., (1979) *Mol. Gen. Genet.* 177:65) encoding the kanamycin resistance gene was cloned into the same sites of pBR322 (Bolivar et al., (1977) *Gene* 2:95) generating pDS7. The Bgl2 site 3' of the kanamycin resistance gene was digested and filled in with the large fragment of *E. coli* DNA polymerase 1 and deoxynucleotides triphosphate. An SstI linker was ligated into the blunted site generating plasmid pCGN1093. Plasmid pPMG34.3 was digested with SalI, the site filled in as above and EcoRI linkers were ligated into the site resulting in plasmid pCGN1092. The letter plasmid was digested with SstI and SmaI and into it was ligated the kanamycin resistance gene excised from pCGN1093 with SstI and SmaI giving pCGN1095. The kanamycin and aroA gene were excised as a piece from pCGN1095 by digestion with SstI and EcoRi and inserted into the SstI and EcoRI sites of pCGN1094 giving pCGN1096. Summarizing, pCGN1096 contains 5' to 3' the following pertinent features: The SSU gene —a polylinker coding for PstI, SalI, SstI, and KpnI —the kanamycin resistance gene —SmaI and BamHI restriction sites —the aroA gene without the original ATG start codon.

A description of the use of Bal31 chewbacks of pCGN1096, as well as a description of pCGN1096 and pCGN566 may be found in Comai, et al., (1988) *J. Biol. Chem.* 263:15104–15109. This manipulation allowed these fragments subsequently to be cloned as BanHI fragments into the BamHI site of pCGN3989 to yield pCGN3992 and pCGN3993 containing the TP and 6 or 12 amino acids of SSU respectively.

PstI fragments from pCGN3989 (d35S-accB-tml3'), pCGN3992 (d35S-TP-SSU+6 amino acids-accB-tml3')and pCGN 3993 (d35S-TP-SSU+12 amino acids-accB-tml3') were cloned into the PstI site of pCGN1547 (McBride and Summerfelt, (1990) *Plant Molec. Biol.* 14:269–276) yielding plasmids pCGN3996, pCGN3995 and pCGN3994. The accB genes in pCGN3996, pCGN3994 and pCGN3995 are transcribed in the same direction as the mas5'-npt-mas3' gene in pCGN1547. Plasmid pCGN1547 is a binary plant transformation vector.

Example 2

Construction of BCCP gene constructs for expression in seeds.

Seed-specific expression of foreign genes is now a well-established technique involving the use of gene expression cassettes engineered for convenience of inserting a DNA sequence comprising a protein- or antisense-coding region for expression in transgenic plants. The fused transit+6/accB sequences in pCGN3992 can be excised as a SalI-SacI fragment which can then be adapted to appropriate sticky end or blunt termini to fit into a seed-specific expression cassette. Alternatively, the fused transit+6/accB coding region can be excised by PCR using primers that add useful restriction sites to the termini of the amplified PCR product.

Example 3

Expression of ACC subunits: TC and BC

Since expression of *E. coli* BCCP is effective in vivo to increase lipid biosynthesis, it follows that comparable engineering of other *E. coli* ACC subunits also will be beneficial. Such engineering can be done exactly as performed for accB: the accA, accc, and accD genes can each be cloned as BamH1-Sac1 fragments using appropriate primers for accA, forward and reverse respectively: CUACUACUAC-UAGGGGATCCTATGAGTCTGAATTTCCTT (SEQ ID NO:10 CAUCAUCAUCAUGAGCTCTTACGCG-TAACCGTAGCT (SEQ ID NO:11 For accc: CUACUAC-UACUAGGGGATCCTATGCTGGATAAAATTGTT (SEQ ID NO:12 CAUCAUCAUCAUGAGCTCTTATTTTTC-CTGAAGACC (SEQ ID NO:13 For accD: CUACUAC-UACUAGGGGATCCTATGAGCTGGATTGAACCA (SEQ ID NO:14 CAUCAUCAUCAUGAGCTCTCAGGC-CTCAGGTTCCTG (SEQ ID NO:15 based on published DNA sequences. Constructs then can be made in similar fashion as that described above for accB using gene expression cassettes such as pCGN2187 (see above) or pCGN3223 (Voelker et al., *Science* 257:72–74). It may be desirable to express accA and accD in the same plant cell host. In such cases, a large binary cassette can be prepared or two different binaries created and two separate transformation steps performed (either into the same plant tissue or into different tissues which are regenerated and later crossed together). Additional selectable markers may be necessary when accA and accD are desired together. Generation and analyses of transgenic plant materials can be done in an analogous manner.

Example 4

Plant Transformation

A variety of methods have been developed to insert a DNA sequence of interest into the genome of a plant host to obtain transcription or transcription and translation of the sequence to effect phenotypic changes.

Brassica Transformation

Seeds of *Brassica napus* cv. Westar are soaked in 95% ethanol for 2 min. surface sterilized in a 1.0% solution of sodium hypochlorite containing a drop of Tween 20 for 45 min., and rinsed three times in sterile, distilled water. Seeds are then plated in Magenta boxes with 1/10th concentration of Murashige minimal organics medium (Gibco; Grand Island, N.Y.) supplemented with pyridoxine (50 µg/l), nicotinic acid (50 µg/l), glycine (200 µg/l), and 0.6% Phytagar (Gibco) pH 5.8. Seeds are germinated in a Percival chamber at 22° C. in a 16 h photoperiod with cool fluorescent and red light of intensity approximately 65 µEinsteins per square meter per second ($\mu Em^{-2}S^{-1}$).

Hypocotyls are excised from 5-7 day old seedlings, cut into pieces approximately 4mm in length, and plated on feeder plates (Horsch et al., (1985) *Science* 227:1229–1231). Feeder plates are prepared one day before use by plating 1.0 ml. of a tobacco suspension culture onto a petri plate (100×25mm) containing about 30 ml MS sale base (Carolina Biological, Burlington, N.C.) 100 mg/l inositol, 1.3 mg/l thiamine-HC1, 200 mg $KH_2PO_4$ with 3% sucrose, 2,4-D (1.0mg/l), 0.6 w/v Phytagar, and pH adjusted to 5.8 prior to autoclaving (MS 0/1/0 medium). A sterile filter paper disc (Whatman 3 mm) is placed on top of the feeder layer prior to use. Tobacco suspension cultures are subcultured weekly by transfer of 10 ml of culture into 100 ml fresh MS medium as described for the feeder plates with 2,4-D (0.2mg/l), Kinetin (0.1mg/l). In experiments where feeder cells are not used hypocotyl explants are cut and placed onto a filter paper disc on top of MS0/1/0 medium. All hypotocol explants are preincubated on feeder plates for 24 h. at 22° C. in continuous light of intensity 30 $\mu Em^{31}\ ^2S^{31}\ ^1$ to 65 $\mu EM^{-2}S^{-1}$.

Single colonies of A. tumefaciens strain EHA 101 containing a binary plasmid are transferred to 5ml MG/L broth and growth overnight at 30° C. Hypocotyl explants are immersed in 7-12 ml MG/L broth with bacteria diluted to 1×10⁸ bacteria/ml and after 10-25 min. are placed onto feeder plates. Per liter MG/L broth contains 5 g mannitol, 1g L-Glutamic acid or 1.15 g sodium glutamate, 0.25 g $kH_2PO_4$, 0.10 g NaCl, 0.10 g $MGSO_4\ 7H_2O$. 1 mg biotin, 5 g tryptone, and 2.5 g yeast extract, and the broth is adjusted to pH 7.0. After 48 hours of co-incubation with Agrobactenium, the hypocotyl explants are transferred to B5 0/1/0 callus induction medium which contains filter sterilized carbenicillin (500 mg/l, added after autoclaving) and kanamycin sulfate (Boehringer Mannheim; Indianapolis, Ind.) at concentrations of 25 mg/l.

After 3-7 days in culture at 65 $\mu EM^{-2}S^{-1}$ continuous light, callus tissue is visible on the cut surface and the hypocotyl explants are transferred to shoot induction medium, B5BZ (B5 salts and vitamins supplemented with 3mg/l benzylaminopurine, 1 mg/l zeatin, 1% sucrose, 0.6% Phytagar and pH adjusted to 5.8). This medium also contains carbenicillin (500 mg/l) and kanamycin sulfate (25 mg/l). Hypotocol explants are subcultured onto fresh shoot induction medium every two weeks.

Shoots regenerate from the hypocotyl calli after one to three months. Green shoots at least 1 cm tall are excised from the calli and placed on medium containing B5 salts and vitamins, 1% sucrose, carbenicillin (300 mg/l), kanamycin sulfate (50 mg/l) and 0.6% w/v Phytagar). After 2-4 weeks shoots which remain green are cut at the base and transferred to Magenta boxes containing root induction medium (B5 salts and vitamins, 1% sucrose, 2 mg/l indolebutyric acid, 50 mg/l kanamycin sulfate and 0.6% Phytagar). Green rooted shoots are tested for kanamycin-resistance enzyme activity.

Example 5

Analysis of Transgenic B. Napus Tissues

Western analysis. *B. napus* plants transformed with plasmids pCGN3994, pCGN3995, pCGN3996 and pCGN1547 were analyzed for expression of the *E. coli* BCCP using a modification of the Western blotting technique. Leaf discs from transgenic plants were obtained from young leaves using a #12 cork borer; the tissue was frozen immediately in liquid nitrogen to prevent protein degradation. Soluble proteins were extracted from leaf discs as follows. One leaf disc (approx. 50 mg fresh weight) was transferred to a 1.5 ml Eppendorf® tube containing 100 µl of extraction buffer (100 mM $NaHPO_4$ (pH6.8), 150 mM NaCl, 10 mM EDTA, 10 mM DTT, 10 mM thiourea, 0.3% Tween-20, 0.05% TritonX-100). The sample was homogenized 5 min. using an electric grinder, and then centrifuged at 4° C. for 5 min. at 16,000×g to remove insoluble material. The supernatant fraction was saved and 200 µg samples of protein from the supernatant were separated by sodium dodecyl sulfate (SDS)-polyacrylamide gel (PAGE) electrophoresis (12% polyacrylamide) (Laemmli, (1970) *Nature* (London) 227:680–685). Proteins were electrophoretically transferred to nitrocellulose (Towbin et al., (1979) *Proc. Natl. Acad. Sci. USA* 76:4350–4354). The nitrocellulose filter was washed for 2 hrs. with TRBS (50 mM TrisHCI (pH 7.5), 200 mM NaCl, 0.5% Tween-20) containing 1% (w/v) skim milk to saturate non-specific protein binding sites. Streptavidin conjugated with alkaline-phosphatase (BRL, Gaithersburg, Md.) was added to a final concentration of 2 µg/ml, and the filter was incubated for 4 hrs. at room temperature with constant shaking. The filter was washed four times with TTBS, once with substrate buffer (0.1 TrisHCl (pH 9.5), 0.1 M NaCl, 50 mM $MgCl_2$) and then incubated with substrate buffer containing 0. 044 mg/ml nitroblue tetrazolium (BRL, Gaithersburg, Md.) and 0. 033 mg/ml 5-bromo-4-chloro-3indolylphosphate (BRL, Gaithersburg, Md.) to detect biotinylated proteins.

Figure 4B:
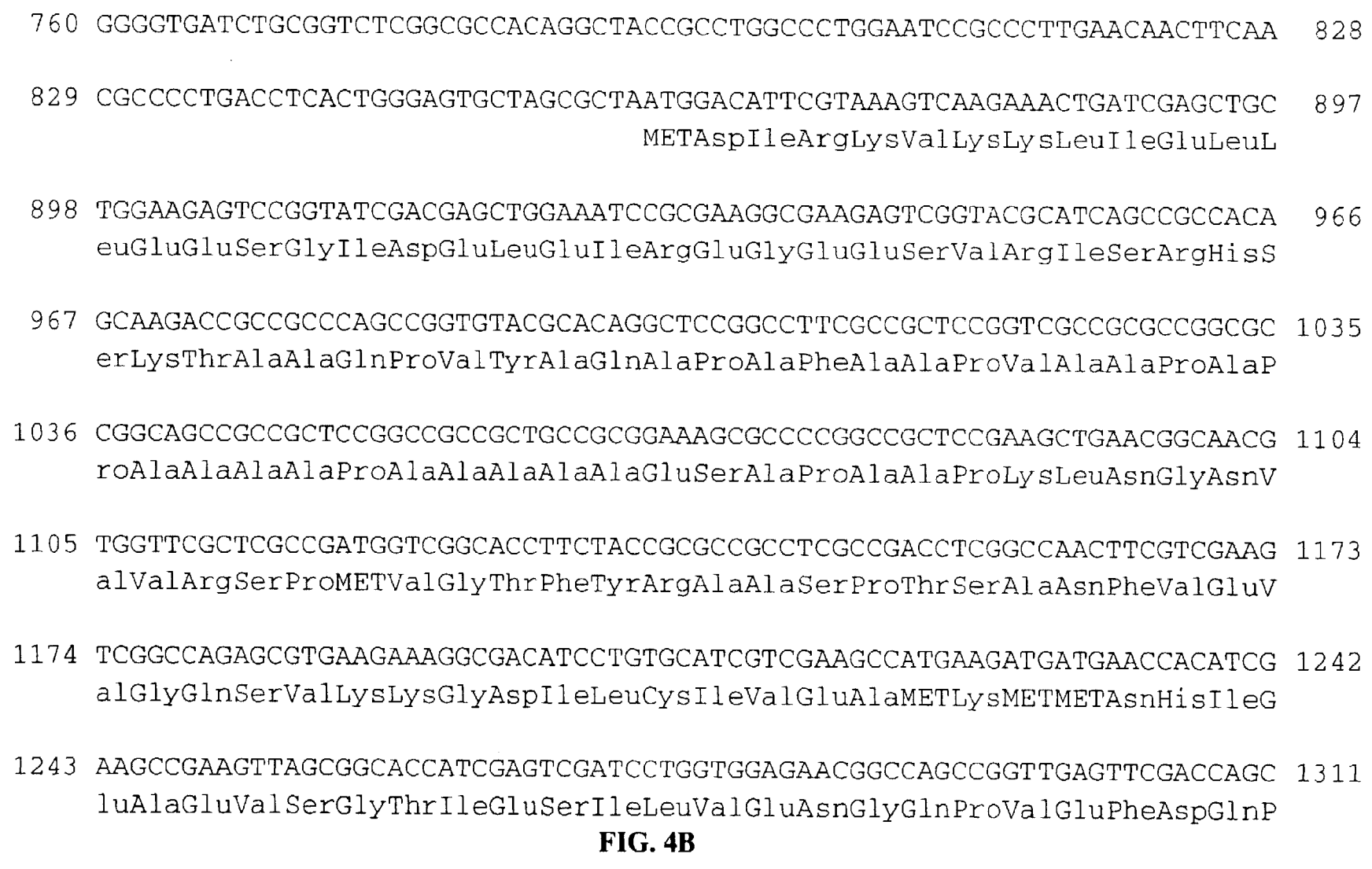

Plants transformed with plasmids pCGN3994, pCGN3995, and pCGN3996 contain biotinylated proteins not present in a control plant containing pCGN1547 (FIG. 4), indicating that the *E. coli* accB is expressed and biotinylated in plants. The largest of the new proteins in extracts from pCGN3994, pCGN3995, and pCGN3996 are 23 kDa, 21 kDa, and 22 kDa respectively, which are consistent with the observed molecular weight of the *E. coli* BCCP, 22 kDa (Li and Cronan, (1992) *J. Biol. Chem.* 267:16841–16847).

Analysis of leaf lipids. Plants were analyzed for changes in fatty acid content and composition using a modification of the method of Browse and coworkers (Browse et aL, (1986) *Anal. Biochem.* 152:141–145). Leaf discs (approx. 200 mg dried wt) punched from *B. napus* leaves were frozen immediately in liquid nitrogen, lyophilized, and then placed in 15 ml screw-capped glass tubes with teflon caps. After addition of 4 ml of methanolic $H_2SO_4$ reagent (5% w/v $H_2SO_4$ in methanol), and 0.25 ml heptadecanoic (17:0) acid (1 mg/ml toluene), the samples were heated for 2 hrs at 90° C., and then cooled at room temperature. 4 ml of 0.9% (w/v) NaCl and 1 ml of hexane were added, and the samples were shaken briefly to extract fatty acid methyl esters into the hexane phase. Samples were centrifuged (1000×g for 1 min) to completely separate the phases, and aliquots (1-2 µl) of the hexane phase was analyzed by gas chromatography. Analysis of fatty acid composition of lipids from *B. napus* leaves is shown in Table 1 (below). Samples 1547-1 and -4 represent transgenic control plants containing no accB constructs. Samples prefixed with 3994, 3995, ad 3996 refer to transgenic rapeseed plants resulting from co-cultivations with Agrobacterium strains containing pCGN3394, pCGN3995, and pCGN3996 respectively. The suffix number (i.e., -10 for sample 3994-10) refers to a specific and unique transformation event. Leaf lipid is expressed as total fatty acids as a percent of dry weight; other percent figures represent relative amounts of major fatty acids found in leaf tissue. Transgenic plants 3995-1, -2, -3 all had unusually high total leaf lipids as well as elevated palmitate levels (C16:0) when compared to controls and other transgenic plants. Event 3995-7 does not appear different than controls; this is apparently due to this transformation event being a relatively poor expressor of the accB gene construct.

used to increase malonyl-CoA. the above noted effects, particularly increases in lipid content, are desirable and possible. Also, as described, increased malonyl-CoA in a target tissue and/or target organelle of interest can be used to further direct and control effects of increased malonyl-CoA. Importantly, it is now discovered that increased malonyl-CoA in plant tissues generally does not appear to affect plant vitality.

Thus, by this invention, production of lipids can be controlled so as to provide a means not only to increase oil yield in seed, but also to increase fruit abscission as a result of increased ethylene production, to increase drought tolerance as a result of increased cuticular wax production, to

TABLE 1

Fatty Acid Composition of Lipids from B. Napus Leaves

| SAMPLE | 16:0 % | 16:1 % | 18:0 % | 18:01 % | 18:2 % | 18:3 % | 20:0 % | 20:1 % | 20:2 % | 22:0 % | 22:1 % | 24:0 % | Leaf Lipid % |
|---|---|---|---|---|---|---|---|---|---|---|---|---|---|
| 1547-1 | 15.9 | 0.1 | 3.2 | 2 | 14.3 | 62 | 0.2 | 0.9 | 0.2 | 0.7 | 0.9 | 0.2 | 2.3 |
| 1547-4 | 15.4 | 0.2 | 2.4 | 2.6 | 15.3 | 60.6 | 0.1 | 0.8 | 0.2 | 0.4 | 1.2 | 0.2 | 2.4 |
| 3994-2 | 15.4 | 0.1 | 2.4 | 2.7 | 17.5 | 59.9 | 0.1 | 0.7 | 0.2 | 0.3 | 1.1 | 0.1 | 3.2 |
| 3994-3 | 15.5 | 0.2 | 3.3 | 2.1 | 12.8 | 62.2 | 0.1 | 1.1 | 0.2 | 0.5 | 1.9 | 0.3 | 2.4 |
| 3994-6 | 14.9 | 0.2 | 3.3 | 2.2 | 13.7 | 62.8 | 0.1 | 1.1 | 0.2 | 0.4 | 0.8 | 0.3 | 2.4 |
| 3994-10 | 16.8 | 0.1 | 3.9 | 2.1 | 12.8 | 60.7 | 0.1 | 1.4 | 0.3 | 0.8 | 1 | 0.4 | 2.3 |
| 3995-1 | 18.2 | 0.4 | 1.9 | 4.7 | 14.7 | 57 | 0.1 | 1 | 0.1 | 0.4 | 1.6 | 0.1 | 4.4 |
| 3995-2 | 19 | 0.4 | 2 | 5.1 | 14.3 | 56.8 | 0.1 | 1 | 0.1 | 0.6 | 0.6 | 0.1 | 4.1 |
| 3995-3 | 17.2 | 1.2 | 2.6 | 3.6 | 16.3 | 56.6 | 0.1 | 1.2 | 0.2 | 0.8 | 1 | 0.1 | 4.3 |
| 3995-7 | 15.3 | 0.3 | 3.1 | 2.3 | 15.2 | 61.1 | 0.1 | 1.2 | 0.2 | 0.7 | 0.5 | 0.2 | 3 |
| 3996-2 | 15.8 | 0.1 | 3.6 | 1.2 | 14.4 | 61.6 | 0.1 | 1.1 | 0.2 | 0.6 | 0 | 0.2 | 2.3 |
| 3996-3 | 15.8 | 0.2 | 3.2 | 0.9 | 13.4 | 62.5 | 0.1 | 1.1 | 0.2 | 0.7 | 0.5 | 0.2 | 3.1 |
| 3996-4 | 16 | 0.2 | 3.4 | 0.9 | 12.1 | 61.9 | 0.2 | 1 | 0.3 | 0.1 | 1.1 | 0.3 | 2.2 |
| 2996-11 | 15 | 0.2 | 3.2 | 0.7 | 13.2 | 63.9 | 0.1 | 1.1 | 0.3 | 0.8 | 0.5 | 0.2 | 3.1 |

As shown in Table 1, three of four independently transformed plants containing pCGN3995 were found to have nearly 2-fold higher amounts of lipids than control plants containing pCGN1547. Plants transformed with pCGN3996 or pCGN3994 had a lipid composition indistinguishable from control plants. These data suggest that the amount of mature SSU is critical for proper expression of the E. coli BCCP and that expression of that protein in the cytoplasm (pCGN3996 plants) does not affect the fatty acid biosynthetic pathway in leaf tissue.

In this invention, we demonstrate that expression of an E. coli gene sequence encoding BCCP in transgenic plants can enhance lipid biosynthesis. The gene product, even though it derives from a prokaryotic source, is correctly biotinylated by the plant cell, and apparently interacts with the plant enzyme to increase malonyl-CoA levels and therefore flux through the fatty acid biosynthetic pathway. The enhancement of fatty acid biosynthesis is observed only with gene constructs that contain transit sequences designed to target the biotinylated BCCP to the chloroplast compartment. However, malonyl-CoA is involved in biosynthesis pathways found in the plant cytoplasm. The combination of this new knowledge relating to enhancement of fatty acid biosynthesis with existing seed-specific gene expression control sequences directly allows the use of BCCP or other E. coli ACC subunit genes to be used in transgenic plants to effect increased levels of malonyl-CoA and to increase lipid biosynthesis in oilseed crops.

Heretofore, it has not been possible to increase the amount of malonyl-CoA in a plant cell. Regardless of the means modify colors influenced by flavonoids and to increase resistance to certain plant pests as a result of increased expression of malonylCo-A-derived phytotoxins in a variety of tissues particularly leaf, fruit and root.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of increasing lipid levels in plant tissue, said method comprising:
growing plant tissue transformed with an expression cassette comprising prokaryotic DNA encoding ACC polypeptide under conditions whereby said ACC polypeptide is produced in an amount sufficient to increase the lipid level over the level in said plant tissue present prior to said increasing.

2. A nucleic acid construct comprising:
in the direction of transcription as functionally linked components, a transcriptional and translational initiation region functional in a plant cell, DNA encoding an enzymatically functional *E. coli* ACC polypeptide, and a transcriptional termination region functional in a plant cell.

3. The nucleic acid construct according to claim 2, wherein said ACC polypeptide is BCCP.

4. The nucleic acid construct according to claim 2, wherein said ACC polypeptide is *E. coli* BCCP.

5. The nucleic acid construct according to claim 2, wherein said transcriptional and translational initiation region comprises a double CaMV 35S promoter.

6. The nucleic acid construct according to claim 2, wherein said transcriptional and translational intiation region comprises a promoter preferentially expressed in one or more specific plant tissues.

7. The nucleic acid construct according to claim 6, wherein said specific plant tissues are selected from the group consisting of leaf, seed, fruit and root.

8. The nucleic acid construct according to claim 2, further comprising operably linked second DNA encoding a translocation peptide which permits transfer of said ACC polypeptide to a chloroplast or proplastid organelle.

9. The nucleic acid construct according to claim 8, wherein said translocation peptide is from a transit peptide of the small subunit of ribulose-1, 5-bisphospate carboxylase.

10. The nucleic acid construct according to claim 9, further comprising operably linked third DNA encoding post-processing amino acids of said ACC polypeptide.

11. A transgenic plant cell comprising a nucleic acid construct according to claim 2.

12. A transgenic plant cell comprising an *E. coli* ACC polypeptide.

13. A transgenic plant cell wherein lipid levels have been increased by the method of claim 1.

14. The transgenic plant cell according to claim 13, wherein said plant cell is a seed cell or a leaf cell.

15. A method of producing an *E. coli* ACC polypeptide in a plant cell, said method comprising:

growing a transgenic host cell or a progeny cell of said transgenic host cell comprising a construct of claim 2 under conditions whereby said *E coli* ACC polypeptide is produced.

16. The method of claim 15, wherein said plant cell is in vivo.

17. A transgenic plant, seed, cell or other plant part comprising:

a nucleic acid constuct according to claim 2.

18. The method according to claim 1, wherein said plant tissue is from *Brassica napus*.

19. The method according to claim 1, wherein said plant tissue is leaf tissue from *Brassica napus*.

20. The nucleic acid construct according to claim 2, wherein said nucleic acid construct is pCGN3995.

21. A method of increasing lipid levels in *Brassic napus* leaf tissue, said method comprising:

growing a *Brassica napus* plant transformed with an expression cassete comprising prokaryotic DNA encoding acetyle CoA carboxylase polypeptide, whereby lipid levels are increased by an amount up to about 87% over the level in said leaf tissue present prior to said increasing.

22. The method according to claim 21, wherein said prokaryotic DNA is from an *E. coli* genome.

23. The method according to claim 21, wherein said expression cassette further comprises plant DNA encoding a peptide comprising a transit peptide and a processing signal.

24. The method according to claim 21, wherein said expressing cassette is pCGN3995.

25. A nucleic acid construct comprising:

in the direction of transcription as fuctionally linked components, a transcriptional and translational initiation region functional in a plant cell, a first DNA encoding a peptide comprising a first peptide region consisting of a transit peptide and processing signal and a second DNA encoding a second peptide region comprising an enzymatically functional *E. coli* ACC polypeptide.

26. The nucleic acid construct according to claim 25, wherein said ACC polypeptide is BCCP.

27. The nucleic acid construct according to claim 25, wherein said transcriptional and translational initiation region comprises a double CaMV 35S promoter.

28. The nucleic acid construct according to claim 25, wherein said transit peptide is from a transit peptide of the small subunit of ribulose-1, 5-bisphosphate carboxylase.

29. The nucleic acid construct according to claim 25, wherein said nucleic acid constuct is pCGN3995.

30. A transgenic plant, seed, cell or other plant part comprising:

a nucleic acid construct according to claim 25.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 3077 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 800..1267

( i x ) FEATURE:
        ( A ) NAME/KEY: CDS
        ( B ) LOCATION: 1281..2626

( x i ) SEQUENCE DESCRIPTION: SEQ ID NO:1:

```
GATACTCCAC TAAACAGCTA TTATTGATAC GCCTCCGTCG CCTGTTAGGT TTATGTTGCT      60

TTGCCTGGGC GCTACGCTTA GCCCCTTACT TATTTCTGGT ACCATGGGGT GAATAATCTG     120

ATTTTGTTTG ACTACAAATT AATCACTCGA ACCTATTTAA TGCTGAGCAT TGTCAATCGG     180

TTAATTTTGC GTGCTTTAGC ATTCACATCT ATCCAGACGA TGCAGTGAAA ATTGGGTAAT     240

CCCCAGCAAC CGCTGCGTAA TGTCGTCTAT CTTGTCGCGA TCCTGGCATC CCTACATTAT     300

TTGTGGTCTG TGAAGATTAT CTCATTGCAG CCCCTCATCT TCGCAGGGCT GGCTTTTCAG     360

CTTTTCACCT TACGTTATAA GAAGTTCCGT CGATGATGGC GCTAATTTCG TGAATTGTGC     420

GGCTTGTTGC AATTACACGG TGTTGAAGGT TATTTCATAG TTAGCTGTTG ATTATCTTCC     480

CTGATAAGAC CAGTATTTAG CTGCCAATTG CTACGAAATC GTTATAATGT GCGACCTCGT     540

CCTCCCTGAC GCAGTTTTTG CGCTGCGGAA AAGGTGACAT GGCGCAACG AAGGTATATT     600

TTGTTTTTTG CCGGAGGATA GCAGCAGATC GCTGCACAAT GTCCGTCAAG TCTAACATTG     660

ACACTCTGGG GCAAAATAGA CCGGCGTCCC GGCCTGCTGG AATTTATCGC TATGCATACA     720

GCTGTCGGGG CATACGCTTT ACAGACGGCG GTGAAACGCC TGTCACAATC ACACTAAACA     780
```

|       |       |       |       |       |       |       |       |       |       |       |       |       |       |       |       |       |
|-------|-------|-------|-------|-------|-------|-------|-------|-------|-------|-------|-------|-------|-------|-------|-------|-------|
| AAGAGTACGG | AACCCACTC | ATG | GAT | ATT | CGT | AAG | ATT | AAA | AAA | CTG | ATC | GAG | | | | 832 |
|       |           | Met | Asp | Ile | Arg | Lys | Ile | Lys | Lys | Leu | Ile | Glu | | | | |
|       |           |  1  |     |     |     |  5  |     |     |     |     |     | 10  | | | | |

| CTG | GTT | GAA | GAA | TCA | GGC | ATC | TCC | GAA | CTG | GAA | ATT | TCT | GAA | GGC | GAA | 880 |
|-----|-----|-----|-----|-----|-----|-----|-----|-----|-----|-----|-----|-----|-----|-----|-----|-----|
| Leu | Val | Glu | Glu | Ser | Gly | Ile | Ser | Glu | Leu | Glu | Ile | Ser | Glu | Gly | Glu | |
|     |     |     |  15 |     |     |     |     |  20 |     |     |     |     |  25 |     |     | |

| GAG | TCA | GTA | CGC | ATT | AGC | CGT | GCA | GCT | CCT | GCC | GCA | AGT | TTC | CCT | GTG | 928 |
| Glu | Ser | Val | Arg | Ile | Ser | Arg | Ala | Ala | Pro | Ala | Ala | Ser | Phe | Pro | Val | |
|     |     |  30 |     |     |     |     |  35 |     |     |     |     |  40 |     |     |     | |

| ATG | CAA | CAA | GCT | TAC | GCT | GCA | CCA | ATG | ATG | CAG | CAG | CCA | GCT | CAA | TCT | 976 |
| Met | Gln | Gln | Ala | Tyr | Ala | Ala | Pro | Met | Met | Gln | Gln | Pro | Ala | Gln | Ser | |
|     |  45 |     |     |     |     |  50 |     |     |     |     |  55 |     |     |     |     | |

| AAC | GCA | GCC | GCT | CCG | GCG | ACC | GTT | CCT | TCC | ATG | GAA | GCG | CCA | GCA | GCA | 1024 |
| Asn | Ala | Ala | Ala | Pro | Ala | Thr | Val | Pro | Ser | Met | Glu | Ala | Pro | Ala | Ala | |
|  60 |     |     |     |     |  65 |     |     |     |     |  70 |     |     |     |     |  75 | |

| GCG | GAA | ATC | AGT | GGT | CAC | ATC | GTA | CGT | TCC | CCG | ATG | GTT | GGT | ACT | TTC | 1072 |
| Ala | Glu | Ile | Ser | Gly | His | Ile | Val | Arg | Ser | Pro | Met | Val | Gly | Thr | Phe | |
|     |     |     |     |  80 |     |     |     |     |  85 |     |     |     |     |  90 |     | |

| TAC | CGC | ACC | CCA | AGC | CCG | GAC | GCA | AAA | GCG | TTC | ATC | GAA | GTG | GGT | CAG | 1120 |
| Tyr | Arg | Thr | Pro | Ser | Pro | Asp | Ala | Lys | Ala | Phe | Ile | Glu | Val | Gly | Gln | |

-continued

| | 95 | | | | | 100 | | | | | 105 | | | | |
|---|---|---|---|---|---|---|---|---|---|---|---|---|---|---|---|

AAA GTC AAC GTG GGC GAT ACC CTG TGC ATC GTT GAA GCC ATG AAA ATG  1168
Lys Val Asn Val Gly Asp Thr Leu Cys Ile Val Glu Ala Met Lys Met
         110              115                 120

ATG AAC CAG ATC GAA GCG GAC AAA TCC GGT ACC GTG AAA GCA ATT CTG  1216
Met Asn Gln Ile Glu Ala Asp Lys Ser Gly Thr Val Lys Ala Ile Leu
    125              130                 135

GTC GAA AGT GGA CAA CCG GTA GAA TTT GAC GAG CCG CTG GTC GTC ATC  1264
Val Glu Ser Gly Gln Pro Val Glu Phe Asp Glu Pro Leu Val Val Ile
140              145                 150                 155

GAG TAACGAGGCG AAC ATG CTG GAT AAA ATT GTT ATT GCC AAC CGC GGC  1313
Glu             Met Leu Asp Lys Ile Val Ile Ala Asn Arg Gly
                  1           5                    10

GAG ATT GCA TTG CGT ATT CTT CGT GCC TGT AAA GAA CTG GGC ATC AAG  1361
Glu Ile Ala Leu Arg Ile Leu Arg Ala Cys Lys Glu Leu Gly Ile Lys
             15              20                  25

ACT GTC GCT GTG CAC TCC AGC GCG GAT CGC GAT CTA AAA CAC GTA TTA  1409
Thr Val Ala Val His Ser Ser Ala Asp Arg Asp Leu Lys His Val Leu
         30                  35                  40

CTG GCA GAT GAA ACG GTC TGT ATT GGC CCT GCT CCG TCA GTA AAA AGT  1457
Leu Ala Asp Glu Thr Val Cys Ile Gly Pro Ala Pro Ser Val Lys Ser
    45                  50                  55

TAT CTG AAC ATC CCG GCA ATC ATC AGC GCC GCT GAA ATC ACC GGC GCA  1505
Tyr Leu Asn Ile Pro Ala Ile Ile Ser Ala Ala Glu Ile Thr Gly Ala
60                  65                  70                  75

GTA GCA ATC CAT CCG GGT TAC GGC TTC CTC TCC GAG AAC GCC AAC TTT  1553
Val Ala Ile His Pro Gly Tyr Gly Phe Leu Ser Glu Asn Ala Asn Phe
             80                  85                  90

GCC GAG CAG GTT GAA CGC TCC GGC TTT ATC TTC ATT GGC CCG AAA GCA  1601
Ala Glu Gln Val Glu Arg Ser Gly Phe Ile Phe Ile Gly Pro Lys Ala
             95                 100                 105

GAA ACC ATT CGC CTG ATG GGC GAC AAA GTA TCC GCA ATC GCG GCG ATG  1649
Glu Thr Ile Arg Leu Met Gly Asp Lys Val Ser Ala Ile Ala Ala Met
         110                 115                 120

AAA AAA GCG GGC GTC CCT TGC GTA CCG GGT TCT GAC GGC CCG CTG GGC  1697
Lys Lys Ala Gly Val Pro Cys Val Pro Gly Ser Asp Gly Pro Leu Gly
125                 130                 135

GAC GAT ATG GAT AAA AAC CGT GCC ATT GCT AAA CGC ATT GGT TAT CCG  1745
Asp Asp Met Asp Lys Asn Arg Ala Ile Ala Lys Arg Ile Gly Tyr Pro
140              145                 150                 155

GTG ATT ATC AAA GCC TCC GGC GGC GGC GGT CGC GGT ATG CGC GTA  1793
Val Ile Ile Lys Ala Ser Gly Gly Gly Gly Arg Gly Met Arg Val
             160                 165                 170

GTG CGC GGC GAC GCT GAA CTG GCA CAA TCC ATC TCC ATG ACC CGT GCG  1841
Val Arg Gly Asp Ala Glu Leu Ala Gln Ser Ile Ser Met Thr Arg Ala
         175                 180                 185

GAA GCG AAA GCT GCT TTC AGC AAC GAT ATG GTT TAC ATG GAG AAA TAC  1889
Glu Ala Lys Ala Ala Phe Ser Asn Asp Met Val Tyr Met Glu Lys Tyr
         190                 195                 200

CTG GAA AAT CCT CGC CAC GTC GAG ATT CAG GTA CTG GCT GAC GGT CAG  1937
Leu Glu Asn Pro Arg His Val Glu Ile Gln Val Leu Ala Asp Gly Gln
    205              210                 215

GGC AAC GCT ATC TAT CTG GCG GAA CGT GAC TGC TCC ATG CAA CGC CGC  1985
Gly Asn Ala Ile Tyr Leu Ala Glu Arg Asp Cys Ser Met Gln Arg Arg
220                 225                 230                 235

CAC CAG AAA GTG GTC GAA GAA GCG CCA GCA CCG GGC ATT ACC CCG GAA  2033
His Gln Lys Val Val Glu Glu Ala Pro Ala Pro Gly Ile Thr Pro Glu
             240                 245                 250

CTG CGT CGC TAC ATC GGC GAA CGT TGC GCT AAA GCG TGT GTT GAT ATC  2081
Leu Arg Arg Tyr Ile Gly Glu Arg Cys Ala Lys Ala Cys Val Asp Ile

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 255 |     |     |     |     | 260 |     |     |     |     | 265 |     |     |      |
| GGC | TAT | CGC | GGT | GCA | GGT | ACT | TTC | GAG | TTC | CTG | TTC | GAA | AAC | GGC | GAG | 2129 |
| Gly | Tyr | Arg | Gly | Ala | Gly | Thr | Phe | Glu | Phe | Leu | Phe | Glu | Asn | Gly | Glu |      |
|     |     | 270 |     |     |     | 275 |     |     |     |     | 280 |     |     |     |     |      |
| TTC | TAT | TTC | ATC | GAA | ATG | AAC | ACC | CGT | ATT | CAG | GTA | GAA | CAC | CCG | GTT | 2177 |
| Phe | Tyr | Phe | Ile | Glu | Met | Asn | Thr | Arg | Ile | Gln | Val | Glu | His | Pro | Val |      |
|     | 285 |     |     |     |     | 290 |     |     |     |     | 295 |     |     |     |     |      |
| ACA | GAA | ATG | ATC | ACC | GGC | GTT | GAC | CTG | ATC | AAA | GAA | CAG | CTG | CGT | ATC | 2225 |
| Thr | Glu | Met | Ile | Thr | Gly | Val | Asp | Leu | Ile | Lys | Glu | Gln | Leu | Arg | Ile |      |
| 300 |     |     |     |     | 305 |     |     |     |     | 310 |     |     |     |     | 315 |      |
| GCT | GCC | GGT | CAA | CCG | CTG | TCG | ATC | AAG | CAA | GAA | GAA | GTT | CAC | GTT | CGC | 2273 |
| Ala | Ala | Gly | Gln | Pro | Leu | Ser | Ile | Lys | Gln | Glu | Glu | Val | His | Val | Arg |      |
|     |     |     |     | 320 |     |     |     |     | 325 |     |     |     |     | 330 |     |      |
| GGC | CAT | GCG | GTG | GAA | TGT | CGT | ATC | AAC | GCC | GAA | GAT | CCG | AAC | ACC | TTC | 2321 |
| Gly | His | Ala | Val | Glu | Cys | Arg | Ile | Asn | Ala | Glu | Asp | Pro | Asn | Thr | Phe |      |
|     |     |     | 335 |     |     |     |     | 340 |     |     |     |     | 345 |     |     |      |
| CTG | CCA | AGT | CCG | GGC | AAA | ATC | ACC | CGT | TTC | CAC | GCA | CCT | GGC | GGT | TTT | 2369 |
| Leu | Pro | Ser | Pro | Gly | Lys | Ile | Thr | Arg | Phe | His | Ala | Pro | Gly | Gly | Phe |      |
|     |     | 350 |     |     |     |     | 355 |     |     |     |     | 360 |     |     |     |      |
| GGC | GTA | CGT | TGG | GAG | TCT | CAT | ATC | TAC | GCG | GGC | TAC | ACC | GTA | CCG | CCG | 2417 |
| Gly | Val | Arg | Trp | Glu | Ser | His | Ile | Tyr | Ala | Gly | Tyr | Thr | Val | Pro | Pro |      |
|     | 365 |     |     |     |     | 370 |     |     |     |     | 375 |     |     |     |     |      |
| TAC | TAT | GAC | TCA | ATG | ATC | GGT | AAG | CTG | ATT | TGC | TAC | GGT | GAA | AAC | CGT | 2465 |
| Tyr | Tyr | Asp | Ser | Met | Ile | Gly | Lys | Leu | Ile | Cys | Tyr | Gly | Glu | Asn | Arg |      |
| 380 |     |     |     |     | 385 |     |     |     |     | 390 |     |     |     |     | 395 |      |
| GAC | GTG | GCG | ATT | GCC | CGC | ATG | AAG | AAT | GCG | CTG | CAG | GAG | CTG | ATC | ATC | 2513 |
| Asp | Val | Ala | Ile | Ala | Arg | Met | Lys | Asn | Ala | Leu | Gln | Glu | Leu | Ile | Ile |      |
|     |     |     | 400 |     |     |     |     | 405 |     |     |     |     | 410 |     |     |      |
| GAC | GGT | ATC | AAA | ACC | AAC | GTT | GAT | CTG | CAG | ATC | CGC | ATC | ATG | AAT | GAC | 2561 |
| Asp | Gly | Ile | Lys | Thr | Asn | Val | Asp | Leu | Gln | Ile | Arg | Ile | Met | Asn | Asp |      |
|     |     |     | 415 |     |     |     |     | 420 |     |     |     |     | 425 |     |     |      |
| GAG | AAC | TTC | CAG | CAT | GGT | GGC | ACT | AAC | ATC | CAC | TAT | CTG | GAG | AAA | AAA | 2609 |
| Glu | Asn | Phe | Gln | His | Gly | Gly | Thr | Asn | Ile | His | Tyr | Leu | Glu | Lys | Lys |      |
|     |     |     | 430 |     |     |     | 435 |     |     |     |     | 440 |     |     |     |      |
| CTC | GGT | CTT | CAG | GAAAAATAAG | | ACTGCTAAAG | | CGTCAAAAGG | | CCGGATTTTC | | | | | | 2661 |
| Leu | Gly | Leu | Gln | Glu |     |     |     |     |     |     |     |     |     |     |     |      |
|     |     | 445 |     |     |     |     |     |     |     |     |     |     |     |     |     |      |

```
CGGCCTTTTT TATTACTGGG GATCGACAAC CCCCATAAGG TACAATCCCC GCTTTCTTCA    2721

CCCATCAGGG ACAAAAAATG GACACTCGTT TTGTTCAGGC CCATAAAGAG GCGCGCTGGG    2781

CGTGGGGCTG ACCCTTTTGT ATCTGGCAGT TTGGTTAGTA GCCGCTTACT TATCTGGCGT    2841

TGCCCCCGGT TTTACCGGCT TTCCGCGCTG GTTTGAGATG GCCTGCATCC TGACGCCGCT    2901

GCTGTTTATT GGACTGTGCT GGGCGATGGT GAAATTTATC TATCGCGATA TCCCACTGGA    2961

GGATGACGAT GCAGCTTGAA GTAATTCTAC CGCTGGTCGC CTATCTGGTG GTGGTGTTCG    3021

GTATCTCGGT TTATGCGATG CGTAAACGGA GCACCGGCAC CTTCCTTAAT GAGTAT        3077
```

( 2 ) INFORMATION FOR SEQ ID NO:2:

( i ) SEQUENCE CHARACTERISTICS:
        ( A ) LENGTH: 156 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Asp | Ile | Arg | Lys | Ile | Lys | Lys | Leu | Ile | Glu | Leu | Val | Glu | Glu | Ser |
| 1   |     |     |     | 5   |     |     |     |     | 10  |     |     |     |     | 15  |     |
| Gly | Ile | Ser | Glu | Leu | Glu | Ile | Ser | Glu | Gly | Glu | Glu | Ser | Val | Arg | Ile |

```
                        20                          25                            30
    Ser  Arg  Ala  Ala  Pro  Ala  Ala  Ser  Phe  Pro  Val  Met  Gln  Gln  Ala  Tyr
              35                         40                       45

Ala  Ala  Pro  Met  Met  Gln  Gln  Pro  Ala  Gln  Ser  Asn  Ala  Ala  Ala  Pro
         50                        55                       60

Ala  Thr  Val  Pro  Ser  Met  Glu  Ala  Pro  Ala  Ala  Ala  Glu  Ile  Ser  Gly
    65                       70                       75                        80

His  Ile  Val  Arg  Ser  Pro  Met  Val  Gly  Thr  Phe  Tyr  Arg  Thr  Pro  Ser
                   85                        90                            95

Pro  Asp  Ala  Lys  Ala  Phe  Ile  Glu  Val  Gly  Gln  Lys  Val  Asn  Val  Gly
                   100                      105                      110

Asp  Thr  Leu  Cys  Ile  Val  Glu  Ala  Met  Lys  Met  Met  Asn  Gln  Ile  Glu
              115                      120                      125

Ala  Asp  Lys  Ser  Gly  Thr  Val  Lys  Ala  Ile  Leu  Val  Glu  Ser  Gly  Gln
         130                      135                      140

Pro  Val  Glu  Phe  Asp  Glu  Pro  Leu  Val  Val  Ile  Glu
    145                      150                      155
```

(2) INFORMATION FOR SEQ ID NO:3:

(i) SEQUENCE CHARACTERISTICS:
        (A) LENGTH: 448 amino acids
        (B) TYPE: amino acid
        (D) TOPOLOGY: linear (ii) MOLECULE TYPE: protein (xi) SEQUENCE DESCRIPTION: SEQ ID NO:3:

```
    Met  Leu  Asp  Lys  Ile  Val  Ile  Ala  Asn  Arg  Gly  Glu  Ile  Ala  Leu  Arg
    1                        5                        10                       15

Ile  Leu  Arg  Ala  Cys  Lys  Glu  Leu  Gly  Ile  Lys  Thr  Val  Ala  Val  His
                   20                       25                       30

Ser  Ser  Ala  Asp  Arg  Asp  Leu  Lys  His  Val  Leu  Leu  Ala  Asp  Glu  Thr
                   35                       40                       45

Val  Cys  Ile  Gly  Pro  Ala  Pro  Ser  Val  Lys  Ser  Tyr  Leu  Asn  Ile  Pro
         50                       55                       60

Ala  Ile  Ile  Ser  Ala  Ala  Glu  Ile  Thr  Gly  Ala  Val  Ala  Ile  His  Pro
    65                       70                       75                        80

Gly  Tyr  Gly  Phe  Leu  Ser  Glu  Asn  Ala  Asn  Phe  Ala  Glu  Gln  Val  Glu
                        85                       90                            95

Arg  Ser  Gly  Phe  Ile  Phe  Ile  Gly  Pro  Lys  Ala  Glu  Thr  Ile  Arg  Leu
                   100                      105                      110

Met  Gly  Asp  Lys  Val  Ser  Ala  Ile  Ala  Ala  Met  Lys  Lys  Ala  Gly  Val
              115                      120                      125

Pro  Cys  Val  Pro  Gly  Ser  Asp  Gly  Pro  Leu  Gly  Asp  Asp  Met  Asp  Lys
         130                      135                      140

Asn  Arg  Ala  Ile  Ala  Lys  Arg  Ile  Gly  Tyr  Pro  Val  Ile  Ile  Lys  Ala
    145                      150                      155                       160

Ser  Gly  Gly  Gly  Gly  Gly  Arg  Gly  Met  Arg  Val  Val  Arg  Gly  Asp  Ala
                        165                      170                      175

Glu  Leu  Ala  Gln  Ser  Ile  Ser  Met  Thr  Arg  Ala  Glu  Ala  Lys  Ala  Ala
              180                      185                      190

Phe  Ser  Asn  Asp  Met  Val  Tyr  Met  Glu  Lys  Tyr  Leu  Glu  Asn  Pro  Arg
         195                      200                      205

His  Val  Glu  Ile  Gln  Val  Leu  Ala  Asp  Gly  Gln  Gly  Asn  Ala  Ile  Tyr
    210                      215                      220
```

| | | | | | | | | | | | | | | | |
|---|---|---|---|---|---|---|---|---|---|---|---|---|---|---|---|
| Leu | Ala | Glu | Arg | Asp | Cys | Ser | Met | Gln | Arg | Arg | His | Gln | Lys | Val | Val |
| 225 | | | | 230 | | | | | 235 | | | | | | 240 |
| Glu | Glu | Ala | Pro | Ala | Pro | Gly | Ile | Thr | Pro | Glu | Leu | Arg | Arg | Tyr | Ile |
| | | | | 245 | | | | | 250 | | | | | 255 | |
| Gly | Glu | Arg | Cys | Ala | Lys | Ala | Cys | Val | Asp | Ile | Gly | Tyr | Arg | Gly | Ala |
| | | | 260 | | | | | 265 | | | | | 270 | | |
| Gly | Thr | Phe | Glu | Phe | Leu | Phe | Glu | Asn | Gly | Glu | Phe | Tyr | Phe | Ile | Glu |
| | | 275 | | | | | 280 | | | | | 285 | | | |
| Met | Asn | Thr | Arg | Ile | Gln | Val | Glu | His | Pro | Val | Thr | Glu | Met | Ile | Thr |
| | 290 | | | | | 295 | | | | | 300 | | | | |
| Gly | Val | Asp | Leu | Ile | Lys | Glu | Gln | Leu | Arg | Ile | Ala | Ala | Gly | Gln | Pro |
| 305 | | | | | 310 | | | | | 315 | | | | | 320 |
| Leu | Ser | Ile | Lys | Gln | Glu | Val | His | Val | Arg | Gly | His | Ala | Val | Glu |
| | | | | 325 | | | | 330 | | | | | 335 | |
| Cys | Arg | Ile | Asn | Ala | Glu | Asp | Pro | Asn | Thr | Phe | Leu | Pro | Ser | Pro | Gly |
| | | | 340 | | | | | 345 | | | | | 350 | | |
| Lys | Ile | Thr | Arg | Phe | His | Ala | Pro | Gly | Gly | Phe | Gly | Val | Arg | Trp | Glu |
| | | 355 | | | | | 360 | | | | | 365 | | | |
| Ser | His | Ile | Tyr | Ala | Gly | Tyr | Thr | Val | Pro | Pro | Tyr | Tyr | Asp | Ser | Met |
| | 370 | | | | | 375 | | | | | 380 | | | | |
| Ile | Gly | Lys | Leu | Ile | Cys | Tyr | Gly | Glu | Asn | Arg | Asp | Val | Ala | Ile | Ala |
| 385 | | | | | 390 | | | | | 395 | | | | | 400 |
| Arg | Met | Lys | Asn | Ala | Leu | Gln | Glu | Leu | Ile | Ile | Asp | Gly | Ile | Lys | Thr |
| | | | | 405 | | | | | 410 | | | | | 415 | |
| Asn | Val | Asp | Leu | Gln | Ile | Arg | Ile | Met | Asn | Asp | Glu | Asn | Phe | Gln | His |
| | | | 420 | | | | | 425 | | | | | 430 | | |
| Gly | Gly | Thr | Asn | Ile | His | Tyr | Leu | Glu | Lys | Lys | Leu | Gly | Leu | Gln | Glu |
| | | 435 | | | | | 440 | | | | | 445 | | | |

( 2 ) INFORMATION FOR SEQ ID NO:4:

( i ) SEQUENCE CHARACTERISTICS:
        ( A ) LENGTH: 3231 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 861..1328

( i x ) FEATURE:
        ( A ) NAME/KEY: CDS
        ( B ) LOCATION: 1349..2695

( x i ) SEQUENCE DESCRIPTION: SEQ ID NO:4:

| | | | | | |
|---|---|---|---|---|---|
| CATCGAGCGC | CAGGTTCTCA | CCGATCCCAC | GGTGCAGGCA | CGACTGCCGG | CCTACCGCCT | 60 |
| GCTGCGCTTC | GACATCACCG | AAAGCAACCC | GGCCAGCGC | GGCCTGCTGG | ACCGCTACAA | 120 |
| CCTGTTCGGT | CCGCCGGCGA | TCCTGTTCTT | CGCCCCGGGC | GGTGACGAAT | GGAGCGACTT | 180 |
| GCGCGTCATC | GGAGAGATCG | ACGCCGCCGG | GCTCGCCGAA | CGACTGCGCC | GGGCCGCTAC | 240 |
| CCGGCAGTGA | CATGCGCTGA | CATACTTCTG | CCGCAATTGC | CGGTCAACAT | GCGGCGATCT | 300 |
| ACTGCAATCT | AACAGTGACT | GGACAGTCAT | ACGGAAATTC | CGGCATAGTG | CCCGCTTGCC | 360 |
| GTTTGCAGCC | TGTACAGGAC | AATCAACAAG | ACAATGGCGA | CCCTCCTCGT | ATTGCACGGG | 420 |
| CCGAATCTGA | ACCTGCTGGG | CACCCGCGAG | CCCGGCACCT | ACGGTTCGAC | CACCCTCGGG | 480 |
| CAGATCAACC | AGGACCTCGA | GCGCCGCGCC | CGCGAAGCCG | GCCACCACCT | GCTGCATCTG | 540 |

```
CAGAGCAACG CCGAATACGA ACTGATCGAC CGGATCCATG CCGCGCGCGA CGAAGGCGTG         600

GACTTCATCA TCATCAATCC GGCGGCATTC ACCCATACCA GCGTCGCGTT ACGTGACGCG         660

CTGCTTGCGG TGAGCATCCC ATTCATCGAA GTGCACCTGT CGAACGTGCA CAAACGTGAA         720

CCTTTCCGGC ATCACTCCTA CTTCTCCGAC GTGGCGGTAG GGGTGATCTG CGGTCTCGGC         780

GCCACAGGCT ACCGCCTGGC CCTGGAATCC GCCCTTGAAC AACTTCAACG CCCCTGACCT         840

CACTGGGAGT GCTAGCGCTA ATG GAC ATT CGT AAA GTC AAG AAA CTG ATC            890
                      Met Asp Ile Arg Lys Val Lys Lys Leu Ile
                       1               5                   10
```

```
GAG CTG CTG GAA GAG TCC GGT ATC GAC GAG CTG GAA ATC CGC GAA GGC           938
Glu Leu Leu Glu Glu Ser Gly Ile Asp Glu Leu Glu Ile Arg Glu Gly
                15                  20                  25

GAA GAG TCG GTA CGC ATC AGC CGC CAC AGC AAG ACC GCC GCC CAG CCG           986
Glu Glu Ser Val Arg Ile Ser Arg His Ser Lys Thr Ala Ala Gln Pro
                30                  35                  40

GTG TAC GCA CAG GCT CCG GCC TTC GCC GCT CCG GTC GCC GCG CCG GCG          1034
Val Tyr Ala Gln Ala Pro Ala Phe Ala Ala Pro Val Ala Ala Pro Ala
            45                  50                  55

CCG GCA GCC GCC GCT CCG GCC GCC GCT GCC GCG GAA AGC GCC CCG GCC          1082
Pro Ala Ala Ala Ala Pro Ala Ala Ala Ala Ala Glu Ser Ala Pro Ala
        60                  65                  70

GCT CCG AAG CTG AAC GGC AAC GTG GTT CGC TCG CCG ATG GTC GGC ACC          1130
Ala Pro Lys Leu Asn Gly Asn Val Val Arg Ser Pro Met Val Gly Thr
75                  80                  85                  90

TTC TAC CGC GCC GCC TCG CCG ACC TCG GCC AAC TTC GTC GAA GTC GGC          1178
Phe Tyr Arg Ala Ala Ser Pro Thr Ser Ala Asn Phe Val Glu Val Gly
                95                  100                 105

CAG AGC GTG AAG AAA GGC GAC ATC CTG TGC ATC GTC GAA GCC ATG AAG          1226
Gln Ser Val Lys Lys Gly Asp Ile Leu Cys Ile Val Glu Ala Met Lys
            110                 115                 120

ATG ATG AAC CAC ATC GAA GCC GAA GTT AGC GGC ACC ATC GAG TCG ATC          1274
Met Met Asn His Ile Glu Ala Glu Val Ser Gly Thr Ile Glu Ser Ile
        125                 130                 135

CTG GTG GAG AAC GGC CAG CCG GTT GAG TTC GAC CAG CCG CTG TTC ACC          1322
Leu Val Glu Asn Gly Gln Pro Val Glu Phe Asp Gln Pro Leu Phe Thr
140                 145                 150

ATC GTC TAAGCCGCGG GGAACCTGCG ATG TTG GAA AAA GTG CTG ATC GCC            1372
Ile Val                       Met Leu Glu Lys Val Leu Ile Ala
155                             1               5

AAC CGC GGC GAA ATC GCC TTG CGC ATC CTT CGC GCA TGC AAG GAG CTG          1420
Asn Arg Gly Glu Ile Ala Leu Arg Ile Leu Arg Ala Cys Lys Glu Leu
        10                  15                  20

GGG ATC AAG ACG GTG GCG GTA CAC TCC ACC GCC GAC CGC GAG TTG ATG          1468
Gly Ile Lys Thr Val Ala Val His Ser Thr Ala Asp Arg Glu Leu Met
25                  30                  35                  40

CAC CTG TCG CTC GCC GAC GAA TCG GTG TGC ATC GGT CCG GCC CCG GCC          1516
His Leu Ser Leu Ala Asp Glu Ser Val Cys Ile Gly Pro Ala Pro Ala
                45                  50                  55

ACC CAG TCG TAC CTG CAG ATC CCG GCG ATC ATC GCC GCG GCC GAG GTC          1564
Thr Gln Ser Tyr Leu Gln Ile Pro Ala Ile Ile Ala Ala Ala Glu Val
            60                  65                  70

ACC GGC GCC ACC GCG ATC CAC CCC GGC TAC GGC TTC CTC GCC GAG AAC          1612
Thr Gly Ala Thr Ala Ile His Pro Gly Tyr Gly Phe Leu Ala Glu Asn
        75                  80                  85

GCC GAC TTC GCC GAG CAG ATC GAA CGC TCC GGC TTC ACC TTC GTC GGC          1660
Ala Asp Phe Ala Glu Gln Ile Glu Arg Ser Gly Phe Thr Phe Val Gly
        90                  95                  100

CCG ACC GCC GAG GTG ATC CGC CTG ATG GGC GAC AAG GTT TCG GCC AAG          1708
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Pro | Thr | Ala | Glu | Val | Ile | Arg | Leu | Met | Gly | Asp | Lys | Val | Ser | Ala | Lys |      |
| 105 |     |     |     |     | 110 |     |     |     | 115 |     |     |     |     |     | 120 |      |
| GAC | GCC | ATG | AAG | CGC | GCC | GGC | GTC | CCC | ACC | GTG | CCG | GGC | TCC | GAC | GGC | 1756 |
| Asp | Ala | Met | Lys | Arg | Ala | Gly | Val | Pro | Thr | Val | Pro | Gly | Ser | Asp | Gly |      |
|     |     |     |     | 125 |     |     |     |     | 130 |     |     |     |     | 135 |     |      |
| CCG | CTG | CCG | GAA | GAT | GAA | GAG | ACC | GCC | CTG | GCG | ATC | GCC | CGC | GAG | GTC | 1804 |
| Pro | Leu | Pro | Glu | Asp | Glu | Glu | Thr | Ala | Leu | Ala | Ile | Ala | Arg | Glu | Val |      |
|     |     |     | 140 |     |     |     |     | 145 |     |     |     |     | 150 |     |     |      |
| GGC | TAC | CCG | GTG | ATC | ATC | AAG | GCC | GCC | GGC | GGC | GGT | GGG | CGC | GGC | | 1852 |
| Gly | Tyr | Pro | Val | Ile | Ile | Lys | Ala | Ala | Gly | Gly | Gly | Gly | Arg | Gly | |      |
|     |     | 155 |     |     |     |     | 160 |     |     |     |     | 165 |     |     | |      |
| ATG | CGC | GTG | GTC | TAC | GAC | GAG | TCC | GAG | CTG | ATC | AAG | TCG | GCC | AAG | CTG | 1900 |
| Met | Arg | Val | Val | Tyr | Asp | Glu | Ser | Glu | Leu | Ile | Lys | Ser | Ala | Lys | Leu |      |
|     | 170 |     |     |     | 175 |     |     |     |     | 180 |     |     |     |     |     |      |
| ACC | CGC | ACC | GAG | GCC | GGC | GCG | GCG | TTC | GGC | AAC | CCG | ATG | GTC | TAC | CTG | 1948 |
| Thr | Arg | Thr | Glu | Ala | Gly | Ala | Ala | Phe | Gly | Asn | Pro | Met | Val | Tyr | Leu |      |
| 185 |     |     |     |     | 190 |     |     |     |     | 195 |     |     |     |     | 200 |      |
| GAG | AAG | TTC | CTG | ACC | AAC | CCG | CGC | CAC | GTG | GAA | GTC | CAG | GTG | CTT | TCC | 1996 |
| Glu | Lys | Phe | Leu | Thr | Asn | Pro | Arg | His | Val | Glu | Val | Gln | Val | Leu | Ser |      |
|     |     |     |     | 205 |     |     |     |     | 210 |     |     |     |     | 215 |     |      |
| GAC | GGC | CAG | GGC | AAC | GCC | ATC | CAC | CTC | GGC | GAC | CGC | GAC | TGC | TCC | CTG | 2044 |
| Asp | Gly | Gln | Gly | Asn | Ala | Ile | His | Leu | Gly | Asp | Arg | Asp | Cys | Ser | Leu |      |
|     |     | 220 |     |     |     |     | 225 |     |     |     |     | 230 |     |     |     |      |
| CAG | CGC | CGC | CAC | CAG | AAG | GTG | ATC | GAA | GAG | GCG | CCG | GCC | CCC | GGC | ATC | 2092 |
| Gln | Arg | Arg | His | Gln | Lys | Val | Ile | Glu | Glu | Ala | Pro | Ala | Pro | Gly | Ile |      |
|     |     | 235 |     |     |     |     | 240 |     |     |     |     | 245 |     |     |     |      |
| GAC | GAG | AAG | GCT | CGC | CAG | GAA | GTC | TTC | GCC | CGC | TGC | GTC | CAG | GCC | TGC | 2140 |
| Asp | Glu | Lys | Ala | Arg | Gln | Glu | Val | Phe | Ala | Arg | Cys | Val | Gln | Ala | Cys |      |
|     |     | 250 |     |     |     | 255 |     |     |     |     | 260 |     |     |     |     |      |
| ATC | GAG | ATC | GGC | TAC | CGC | GGC | GCC | GGC | ACC | TTC | GAG | TTC | CTC | TAC | GAG | 2188 |
| Ile | Glu | Ile | Gly | Tyr | Arg | Gly | Ala | Gly | Thr | Phe | Glu | Phe | Leu | Tyr | Glu |      |
| 265 |     |     |     |     | 270 |     |     |     |     | 275 |     |     |     |     | 280 |      |
| AAC | GGC | CGC | TTC | TAC | TTC | ATC | GAG | ATG | AAC | ACT | CGC | GTG | CAG | GTG | GAG | 2236 |
| Asn | Gly | Arg | Phe | Tyr | Phe | Ile | Glu | Met | Asn | Thr | Arg | Val | Gln | Val | Glu |      |
|     |     |     |     | 285 |     |     |     |     | 290 |     |     |     |     | 295 |     |      |
| CAC | CCG | GTA | TCT | GAG | ATG | GTC | ACC | GGT | GTC | GAC | ATC | GTC | AAG | GAG | ATG | 2284 |
| His | Pro | Val | Ser | Glu | Met | Val | Thr | Gly | Val | Asp | Ile | Val | Lys | Glu | Met |      |
|     |     |     | 300 |     |     |     |     | 305 |     |     |     |     | 310 |     |     |      |
| CTG | CGC | ATC | GCC | TCC | GGC | GAG | AAG | CTC | TCG | ATC | CGC | CAG | GAG | GAC | GTG | 2332 |
| Leu | Arg | Ile | Ala | Ser | Gly | Glu | Lys | Leu | Ser | Ile | Arg | Gln | Glu | Asp | Val |      |
|     |     | 315 |     |     |     |     | 320 |     |     |     |     | 325 |     |     |     |      |
| GTC | ATC | CGC | GGC | CAT | GCG | CTG | GAA | TGC | CGG | ATC | AAC | GCC | GAA | GAC | CCG | 2380 |
| Val | Ile | Arg | Gly | His | Ala | Leu | Glu | Cys | Arg | Ile | Asn | Ala | Glu | Asp | Pro |      |
|     | 330 |     |     |     |     | 335 |     |     |     |     | 340 |     |     |     |     |      |
| AAG | ACC | TTC | ATG | CCC | AGC | CCG | GGC | AAG | GTC | AAG | CAC | TTC | CAC | GCC | CCC | 2428 |
| Lys | Thr | Phe | Met | Pro | Ser | Pro | Gly | Lys | Val | Lys | His | Phe | His | Ala | Pro |      |
| 345 |     |     |     |     | 350 |     |     |     |     | 355 |     |     |     |     | 360 |      |
| GGC | GGC | AAC | GGC | GTG | CGC | GTC | GAC | TCG | CAC | CTC | TAC | AGC | GGC | TAC | AGC | 2476 |
| Gly | Gly | Asn | Gly | Val | Arg | Val | Asp | Ser | His | Leu | Tyr | Ser | Gly | Tyr | Ser |      |
|     |     |     |     | 365 |     |     |     |     | 370 |     |     |     |     | 375 |     |      |
| GTG | CCG | CCG | AAC | TAC | GAC | TCG | CTG | GTC | GGC | AAG | GTC | ATC | ACC | TAC | GGT | 2524 |
| Val | Pro | Pro | Asn | Tyr | Asp | Ser | Leu | Val | Gly | Lys | Val | Ile | Thr | Tyr | Gly |      |
|     |     |     | 380 |     |     |     |     | 385 |     |     |     |     | 390 |     |     |      |
| GCC | GAC | CGC | GAC | GAG | GCG | CTG | GCG | CGG | ATG | CGC | AAT | GCC | CTG | GAC | GAG | 2572 |
| Ala | Asp | Arg | Asp | Glu | Ala | Leu | Ala | Arg | Met | Arg | Asn | Ala | Leu | Asp | Glu |      |
|     |     | 395 |     |     |     |     | 400 |     |     |     |     | 405 |     |     |     |      |
| TTG | ATC | GTC | GAC | GGT | ATC | AAG | ACC | AAT | ACC | GAA | CTG | CAC | AAG | GAC | CTG | 2620 |
| Leu | Ile | Val | Asp | Gly | Ile | Lys | Thr | Asn | Thr | Glu | Leu | His | Lys | Asp | Leu |      |
|     | 410 |     |     |     |     | 415 |     |     |     |     | 420 |     |     |     |     |      |
| GTG | CGC | GAC | GCC | GCC | TTC | TGC | AAG | GGC | GGG | GTG | AAC | ATC | CAT | TAC | CTG | 2668 |

| | | | | | | | | | | | | | | |
|---|---|---|---|---|---|---|---|---|---|---|---|---|---|---|
| Val | Arg | Asp | Ala | Ala | Phe | Cys | Lys | Gly | Gly | Val | Asn | Ile | His | Tyr | Leu |
| 425 | | | | 430 | | | | | 435 | | | | | 440 |

| | | | | | | | | |
|---|---|---|---|---|---|---|---|---|
| GAG | AAG | AAA | CTG | GGT | ATG | GAC | AAG | CAC | TGATCCGTCA GTCGCTGCGC | 2715 |
| Glu | Lys | Lys | Leu | Gly | Met | Asp | Lys | His | | |
| | | | | 445 | | | | | | |

| | | | | |
|---|---|---|---|---|
| ACAAGGGCTG | CCTCCGGGCG | GCCCTTGTCG | TTTCCGCCTG | CCGGCCGCCC | AACGGTGCT | 2775 |
| ATCCTCGTCG | CCCCTCCACC | ACCGGACTCC | TGCATGGAAC | GCATCCGCCG | CTGGTACCGC | 2835 |
| CAATCGCTGG | CCGCCGCGAC | CGAGGCCGCG | ACCTGCTTCG | CCCTGGGTTT | CAGGGAAAGC | 2895 |
| CTGCAACCCG | CCGCACTCTT | CCGCTCCGCG | AGCCTGTGCA | TTCTCGTCAG | CGTGCTGTGC | 2955 |
| ACCTGGCTGT | TCGTGCATTT | CTTCGAACCG | ATCATCCGCC | TCTGCGGCTG | GGCCGCGCTG | 3015 |
| TACACGGCAT | TCAGCGTGGC | CAACTTCGCC | CTGATCCCCA | GCGGCTCGCT | GATCGAGGCC | 3075 |
| GGCAGCGGTG | GCCCGTACTT | CGATCCGCTG | GCGGCCTTCA | ACGGCCTGGC | GGGACTGGCG | 3135 |
| CAACTGGCGT | TCTATTTCGT | CGGCTATGCC | GCGCTGTTCT | TCGTCGCCCT | GTACGCCGCC | 3195 |
| AGCATCGTCT | TCGGCATCCG | CCTGGGCCTG | CGCATC | | | 3231 |

(2) INFORMATION FOR SEQ ID NO:5:

(i) SEQUENCE CHARACTERISTICS:
        (A) LENGTH: 156 amino acids
        (B) TYPE: amino acid
        (D) TOPOLOGY: linear (ii) MOLECULE TYPE: protein (xi) SEQUENCE DESCRIPTION: SEQ ID NO:5:

| | | | | | | | | | | | | | | | |
|---|---|---|---|---|---|---|---|---|---|---|---|---|---|---|---|
| Met | Asp | Ile | Arg | Lys | Val | Lys | Lys | Leu | Ile | Glu | Leu | Leu | Glu | Glu | Ser |
| 1 | | | | 5 | | | | | 10 | | | | | 15 | |
| Gly | Ile | Asp | Glu | Leu | Glu | Ile | Arg | Glu | Gly | Glu | Glu | Ser | Val | Arg | Ile |
| | | | 20 | | | | | 25 | | | | | 30 | | |
| Ser | Arg | His | Ser | Lys | Thr | Ala | Ala | Gln | Pro | Val | Tyr | Ala | Gln | Ala | Pro |
| | | | 35 | | | | 40 | | | | | 45 | | | |
| Ala | Phe | Ala | Ala | Pro | Val | Ala | Ala | Pro | Ala | Pro | Ala | Ala | Ala | Ala | Pro |
| | | 50 | | | | | 55 | | | | | 60 | | | |
| Ala | Ala | Ala | Ala | Ala | Glu | Ser | Ala | Pro | Ala | Ala | Pro | Lys | Leu | Asn | Gly |
| 65 | | | | | 70 | | | | | 75 | | | | | 80 |
| Asn | Val | Val | Arg | Ser | Pro | Met | Val | Gly | Thr | Phe | Tyr | Arg | Ala | Ala | Ser |
| | | | | 85 | | | | | 90 | | | | | 95 | |
| Pro | Thr | Ser | Ala | Asn | Phe | Val | Glu | Val | Gly | Gln | Ser | Val | Lys | Lys | Gly |
| | | | | 100 | | | | | 105 | | | | | 110 | |
| Asp | Ile | Leu | Cys | Ile | Val | Glu | Ala | Met | Lys | Met | Met | Asn | His | Ile | Glu |
| | | | 115 | | | | | 120 | | | | | 125 | | |
| Ala | Glu | Val | Ser | Gly | Thr | Ile | Glu | Ser | Ile | Leu | Val | Glu | Asn | Gly | Gln |
| | | | 130 | | | | | 135 | | | | | 140 | | |
| Pro | Val | Glu | Phe | Asp | Gln | Pro | Leu | Phe | Thr | Ile | Val | | | | |
| 145 | | | | | 150 | | | | | 155 | | | | | |

(2) INFORMATION FOR SEQ ID NO:6:

(i) SEQUENCE CHARACTERISTICS:
        (A) LENGTH: 449 amino acids
        (B) TYPE: amino acid
        (D) TOPOLOGY: linear (ii) MOLECULE TYPE: protein (xi) SEQUENCE DESCRIPTION: SEQ ID NO:6:

| | | | | | | | | | | | | | | | |
|---|---|---|---|---|---|---|---|---|---|---|---|---|---|---|---|
| Met | Leu | Glu | Lys | Val | Leu | Ile | Ala | Asn | Arg | Gly | Glu | Ile | Ala | Leu | Arg |

```
  1                    5                              10                          15

Ile  Leu  Arg  Ala  Cys  Lys  Glu  Leu  Gly  Ile  Lys  Thr  Val  Ala  Val  His
              20                        25                        30

Ser  Thr  Ala  Asp  Arg  Glu  Leu  Met  His  Leu  Ser  Leu  Ala  Asp  Glu  Ser
              35                        40                        45

Val  Cys  Ile  Gly  Pro  Ala  Pro  Ala  Thr  Gln  Ser  Tyr  Leu  Gln  Ile  Pro
         50                        55                        60

Ala  Ile  Ile  Ala  Ala  Ala  Glu  Val  Thr  Gly  Ala  Thr  Ala  Ile  His  Pro
65                             70                        75                        80

Gly  Tyr  Gly  Phe  Leu  Ala  Glu  Asn  Ala  Asp  Phe  Ala  Glu  Gln  Ile  Glu
                        85                        90                        95

Arg  Ser  Gly  Phe  Thr  Phe  Val  Gly  Pro  Thr  Ala  Glu  Val  Ile  Arg  Leu
                   100                       105                       110

Met  Gly  Asp  Lys  Val  Ser  Ala  Lys  Asp  Ala  Met  Lys  Arg  Ala  Gly  Val
              115                       120                       125

Pro  Thr  Val  Pro  Gly  Ser  Asp  Gly  Pro  Leu  Pro  Glu  Asp  Glu  Glu  Thr
         130                       135                       140

Ala  Leu  Ala  Ile  Ala  Arg  Glu  Val  Gly  Tyr  Pro  Val  Ile  Ile  Lys  Ala
145                            150                       155                       160

Ala  Gly  Gly  Gly  Gly  Gly  Arg  Gly  Met  Arg  Val  Val  Tyr  Asp  Glu  Ser
                        165                       170                       175

Glu  Leu  Ile  Lys  Ser  Ala  Lys  Leu  Thr  Arg  Thr  Glu  Ala  Gly  Ala  Ala
              180                       185                       190

Phe  Gly  Asn  Pro  Met  Val  Tyr  Leu  Glu  Lys  Phe  Leu  Thr  Asn  Pro  Arg
              195                       200                       205

His  Val  Glu  Val  Gln  Val  Leu  Ser  Asp  Gly  Gln  Gly  Asn  Ala  Ile  His
         210                       215                       220

Leu  Gly  Asp  Arg  Asp  Cys  Ser  Leu  Gln  Arg  Arg  His  Gln  Lys  Val  Ile
225                            230                       235                       240

Glu  Glu  Ala  Pro  Ala  Pro  Gly  Ile  Asp  Glu  Lys  Ala  Arg  Gln  Glu  Val
                   245                       250                       255

Phe  Ala  Arg  Cys  Val  Gln  Ala  Cys  Ile  Glu  Ile  Gly  Tyr  Arg  Gly  Ala
              260                       265                       270

Gly  Thr  Phe  Glu  Phe  Leu  Tyr  Glu  Asn  Gly  Arg  Phe  Tyr  Phe  Ile  Glu
         275                       280                       285

Met  Asn  Thr  Arg  Val  Gln  Val  Glu  His  Pro  Val  Ser  Glu  Met  Val  Thr
290                            295                       300

Gly  Val  Asp  Ile  Val  Lys  Glu  Met  Leu  Arg  Ile  Ala  Ser  Gly  Glu  Lys
305                            310                       315                       320

Leu  Ser  Ile  Arg  Gln  Glu  Asp  Val  Val  Ile  Arg  Gly  His  Ala  Leu  Glu
                   325                       330                       335

Cys  Arg  Ile  Asn  Ala  Glu  Asp  Pro  Lys  Thr  Phe  Met  Pro  Ser  Pro  Gly
              340                       345                       350

Lys  Val  Lys  His  Phe  His  Ala  Pro  Gly  Gly  Asn  Gly  Val  Arg  Val  Asp
              355                       360                       365

Ser  His  Leu  Tyr  Ser  Gly  Tyr  Ser  Val  Pro  Pro  Asn  Tyr  Asp  Ser  Leu
         370                       375                       380

Val  Gly  Lys  Val  Ile  Thr  Tyr  Gly  Ala  Asp  Arg  Asp  Glu  Ala  Leu  Ala
385                            390                       395                       400

Arg  Met  Arg  Asn  Ala  Leu  Asp  Glu  Leu  Ile  Val  Asp  Gly  Ile  Lys  Thr
                   405                       410                       415

Asn  Thr  Glu  Leu  His  Lys  Asp  Leu  Val  Arg  Asp  Ala  Ala  Phe  Cys  Lys
              420                       425                       430
```

| Gly | Gly | Val | Asn | Ile | His | Tyr | Leu | Glu | Lys | Lys | Leu | Gly | Met | Asp | Lys |
|-----|-----|-----|-----|-----|-----|-----|-----|-----|-----|-----|-----|-----|-----|-----|-----|
|     |     | 435 |     |     |     |     | 440 |     |     |     |     | 445 |     |     |     |

His ( 2 ) INFORMATION FOR SEQ ID NO:7:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA/RNA hybrid ( x i ) SEQUENCE DESCRIPTION: SEQ ID NO:7:

CUACUACUAC UAGGGGATCC TATGGATATT CGTAAGATT         39

( 2 ) INFORMATION FOR SEQ ID NO:8:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA/RNA hybrid ( x i ) SEQUENCE DESCRIPTION: SEQ ID NO:8:

CAUCAUCAUC AUGAGCTCTT ACTCGATGAC GACCAG         36

( 2 ) INFORMATION FOR SEQ ID NO:9:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA/RNA hybrid ( x i ) SEQUENCE DESCRIPTION: SEQ ID NO:9:

ACAATGCATG CCGGATCCCG TGACTTTCAT GGAA         34

( 2 ) INFORMATION FOR SEQ ID NO:10:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA/RNA hybrid ( x i ) SEQUENCE DESCRIPTION: SEQ ID NO:10:

CUACUACUAC UAGGGGATCC TATGAGTCTG AATTTCCTT         39

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA/RNA hybrid ( x i ) SEQUENCE DESCRIPTION: SEQ ID NO:11:

CAUCAUCAUC AUGAGCTCTT ACGCGTAACC GTAGCT         36

(2) INFORMATION FOR SEQ ID NO:12:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA/RNA hybrid (xi) SEQUENCE DESCRIPTION: SEQ ID NO:12:

CUACUACUAC UAGGGGATCC TATGCTGGAT AAAATTGTT  39

(2) INFORMATION FOR SEQ ID NO:13:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA/RNA hybrid (xi) SEQUENCE DESCRIPTION: SEQ ID NO:13:

CAUCAUCAUC AUGAGCTCTT ATTTTCCTG AAGACC  36

(2) INFORMATION FOR SEQ ID NO:14:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA/RNA hybrid (xi) SEQUENCE DESCRIPTION: SEQ ID NO:14:

CUACUACUAC UAGGGGATCC TATGAGCTGG ATTGAACCA  39

(2) INFORMATION FOR SEQ ID NO:15:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA/RNA hybrid (xi) SEQUENCE DESCRIPTION: SEQ ID NO:15:

CAUCAUCAUC AUGAGCTCTC AGGCCTCAGG TTCCTG  36